US010317407B2

(12) United States Patent
Rak et al.

(10) Patent No.: US 10,317,407 B2
(45) Date of Patent: *Jun. 11, 2019

(54) TUMOR CELL-DERIVED MICROVESICLES

(71) Applicants: The Hospital for Sick Children, Toronto (CA); The Royal Institution for the Advancement of Learning/McGill University, Montreal (CA)

(72) Inventors: Janusz Rak, Montreal (CA); Khalid Al-Nedawi, St-Lambert (CA); Brian Meehan, Montreal (CA); Abhijit Guha, Toronto (CA)

(73) Assignees: THE ROYAL INSTITUTION FOR THE ADVANCEMENT OF LEARNING/MCGILL UNIVERSITY, Montreal, Quebec (CA); THE HOSPITAL FOR SICK CHILDREN, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/927,392

(22) Filed: Oct. 29, 2015

(65) Prior Publication Data

US 2016/0245812 A1 Aug. 25, 2016

Related U.S. Application Data

(63) Continuation of application No. 12/673,528, filed as application No. PCT/CA2008/001441 on Aug. 8, 2008, now Pat. No. 9,186,405.

(60) Provisional application No. 60/935,505, filed on Aug. 16, 2007.

(51) Int. Cl.
| | |
|---|---|
| G01N 33/573 | (2006.01) |
| G01N 33/574 | (2006.01) |
| A61K 45/06 | (2006.01) |
| A61B 10/00 | (2006.01) |

(52) U.S. Cl.
CPC ......... *G01N 33/5748* (2013.01); *A61K 45/06* (2013.01); *G01N 33/57488* (2013.01); *A61B 10/0045* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,685,911 | B1 | 2/2004 | Zitvogel et al. |
| 6,812,023 | B1 | 11/2004 | Zitvogel et al. |
| 6,899,863 | B1 | 5/2005 | Dhellin et al. |
| 7,005,271 | B1 | 2/2006 | Freyssinet et al. |
| 7,462,489 | B2 | 12/2008 | Ley et al. |
| 7,732,148 | B2 | 6/2010 | Cahill et al. |
| 7,888,035 | B2 | 2/2011 | Klass et al. |
| 7,897,356 | B2 | 3/2011 | Klass et al. |
| 9,186,405 | B2 | 11/2015 | Rak et al. |
| 2005/0130241 | A1 | 6/2005 | Carlsson et al. |
| 2007/0141066 | A1 | 6/2007 | Phillips et al. |
| 2007/0172900 | A1 | 7/2007 | Cahill et al. |
| 2009/0220944 | A1 | 9/2009 | Fais et al. |
| 2009/0258379 | A1 | 10/2009 | Klein et al. |
| 2010/0151480 | A1 | 6/2010 | Taylor et al. |
| 2010/0196426 | A1 | 8/2010 | Skog et al. |
| 2010/0239572 | A1 | 9/2010 | Rotolo et al. |
| 2010/0255514 | A1 | 10/2010 | Rak et al. |
| 2010/0298151 | A1 | 11/2010 | Taylor et al. |
| 2011/0003704 | A1 | 1/2011 | Skog et al. |
| 2016/0245812 | A1 | 8/2016 | Rak et al. |

FOREIGN PATENT DOCUMENTS

| | | |
|---|---|---|
| EP | 0772778 A1 | 5/1997 |
| EP | 1902732 A1 | 3/2008 |
| EP | 2176665 B1 | 3/2016 |
| GB | 2463401 A | 3/2010 |
| JP | 03505250 A | 11/1991 |
| JP | 7-508749 A | 9/1995 |
| JP | 2001-508303 A | 6/2001 |
| JP | 2003-525866 A | 9/2003 |
| JP | 2007-527001 A | 9/2007 |
| JP | 2007-537700 A | 12/2007 |
| JP | 2009-501516 A | 1/2009 |
| JP | 2013-524247 A | 6/2013 |
| WO | 1994/01458 A1 | 1/1994 |
| WO | 2001/082958 A2 | 11/2001 |
| WO | 2003/011330 A1 | 2/2003 |
| WO | 2005/003156 A1 | 1/2005 |
| WO | 2005/056764 A2 | 6/2005 |
| WO | 2005/078124 A2 | 8/2005 |
| WO | 2005/121369 A2 | 12/2005 |
| WO | 2006/087233 A2 | 8/2006 |
| WO | 2006/137595 A1 | 12/2006 |

(Continued)

OTHER PUBLICATIONS

Wlkstrand et al Cancer Res, 57: 4130-4140, 1997 (Year: 1997).*
Okamoto et al, Cancer Sci 94:50-56, 2003 (Year: 2003).*
Lu et al., "Epidermal Growth Factor-Induced Tumor Cell Invasion and Metastasis Initiated by Dephosphorylation and Downregulation of Focal Adhesion Kinase", Molecular and Cellular Biology, vol. 21, No. 12, Jun. 2001, pp. 4016-4031.
Pasquet et al., "Microvesicle Release is Associated with Extensive Protein Tyrosine Dephosphorylation in Platelets Stimulated by A23187 or a Mixture of Thrombin and Collagen", Biochem. J., vol. 333, 1998, pp. 591-599.

(Continued)

*Primary Examiner* — Lei Yao
(74) *Attorney, Agent, or Firm* — Morrison & Foerster LLP

(57) ABSTRACT

The present invention relates to a method for diagnosis of cancer and for monitoring the progression of cancer and/or the therapeutic efficacy of an anti-cancer treatment in a sample of a subject by detecting oncogenic proteins in microvesicles, and to the use of an agent blocking exchange of microvesicles for treating cancer.

12 Claims, 7 Drawing Sheets

(56) References Cited

FOREIGN PATENT DOCUMENTS

| WO | 2007/009613 | A1 | 1/2007 |
|---|---|---|---|
| WO | 2007/103572 | A2 | 9/2007 |
| WO | 2007/127848 | A1 | 11/2007 |
| WO | 2008/060896 | A2 | 5/2008 |
| WO | 2008/088747 | A2 | 7/2008 |
| WO | 2008/125262 | A1 | 10/2008 |
| WO | 2009/015357 | A1 | 1/2009 |
| WO | 2009/019215 | A1 | 2/2009 |
| WO | 2009/021322 | A1 | 2/2009 |
| WO | 2009/036236 | A1 | 3/2009 |
| WO | 2009/092386 | A2 | 7/2009 |
| WO | 2009/100029 | A1 | 8/2009 |
| WO | 2009/124391 | A1 | 10/2009 |
| WO | 2009/147519 | A1 | 12/2009 |
| WO | 2009/155505 | A2 | 12/2009 |
| WO | 2010/028313 | A2 | 3/2010 |
| WO | 2010/056337 | A2 | 5/2010 |
| WO | 2010/062706 | A2 | 6/2010 |
| WO | 2010/065765 | A2 | 6/2010 |
| WO | 2010/065968 | A1 | 6/2010 |
| WO | 2010/141955 | A2 | 12/2010 |
| WO | 2011/127585 | A1 | 10/2011 |

OTHER PUBLICATIONS

Abdullah et al., "Microparticle Surface Proteins are Associated with Experimental Venous Thrombosis: A Preliminary Study", Clin Appl Thromb Hemost, vol. 15, No. 2, 2009, pp. 201-208.
Abraham et al., "Epithelial Ovarian Cancer Cells Secrete Functional Fas Ligand", Cancer Research, vol. 63, 2003, pp. 5573-5581.
Aharon et al., "Microparticles, Thrombosis and Cancer", Best. Pract. Res. Clin Haematol, vol. 22, 2009, pp. 61-69.
Ahmed et al., "Mechanisms of Cellular Communication Through Intercellular Protein Transfer", J. Cell Mol. Med., vol. 15, No. 7, Jul. 2011, pp. 1458-1473.
Al-Nedawi et al., "Endothelial Expression of Autocrine VEGF upon the Uptake of Tumor-Derived Microvesicles Containing Oncogenic EGFR", Proc. Natl. Acad. Sci. U.S.A, vol. 106, 2009, pp. 3794-3799.
Al-Nedawi et al., "Intercellular Transfer of the Oncogenic Receptor EGFRvIII by Microvesicles Derived from Tumour Cells", Nat. Cell Biol., vol. 10, 2008, pp. 619-624.
Al-Nedawi et al., "Microvesicles: Messengers and Mediators of Tumor Progression", Cell Cycle, vol. 8, No. 13, 2009, pp. 2014-2018.
Albanese et al., "Biologically Active Fas Antigen and Its Cognate Ligand are Expressed on Plasma Membrane-Derived Extracellular Vesicles", Blood, vol. 91, No. 10, 2010, pp. 3862-3874.
Andre et al., "Exosomes as Potent Cell-Free Peptide-Based Vaccine. I. Dendritic Celi- Derived Exosomes Transfer Functional MHC Class IIPeptide Complexes to Dendritic Cells", The Journal of Immunology, vol. 172, 2004, pp. 2126-2136.
Andre et al., "Malignant Effusions and Immunogenic Tumour-Derived Exosomes", Lancet, vol. 360, No. 9329, Jul. 2002, pp. 295-305.
Andreola et al., "Induction of Lymphocyte Apoptosis by Tumor Cell Secretion of FasL-Bearing Microvesicles", J. Exp. Med., vol. 195, 2002, pp. 1303-1316.
Angelucci et al., "Vesicle-Associated Urokinase Plasminogen Activator Promotes Invasion in Prostate Cancer Cell Lines", Clin Exp. Metastasis, vol. 18, 2000, pp. 163-170.
Baj-Krzyworzeka et al., "Tumour-Derived Microvesicles Carry Several Surface Determinants and MRNA of Tumour Cells and Transfer Some of these Determinants to Monocytes", Cancer Immunoloqy and Immunotherapy, vol. 55, 2006, pp. 808-818.
Baj-Krzyworzeka, "Platelet-Derived Microparticles Stimulate Proliferation, Survival, Adhesion, and Chemotaxis of Hematopoietic Cells", Exp. Hematol. vol. 30, 2002, pp. 450-459.

Balaj et al., "Tumour Microvesicles contain Retrotransposon Elements and Amplified Oncocene Sequences", Nat. Commun, vol. 2, No. 180, 2011, 1 page.
Bard et al., "Proteomic Analysis of Exosomes Isolated from Human Malignant Pleural Effusions", Am J Respir Cell Mol Biol. vol. 31, No. 1, Jul. 2004, pp. 114-121.
Bastida et al., "Tissue Factor in Microvesicles Shed from U87MG Human Glioblastoma Cells Induces Coagulation, Platelet Aggregation, and Thrombogenesis", Blood, vol. 64, No. 1, Jul. 1984, pp. 177-184.
Bergmann et al., "Tumor-Derived Microvesicles in Sera of Patients with Head and Neck Cancer and their Role in Tumor Progression", Head Neck, vol. 31, 2009, pp. 371-380.
Bergsmedh et al., "Horizontal Transfer of Oncogenes by Uptake of Apoptotic Bodies", Proc Natl Acad Sci USA, vol. 98, 2001, pp. 6407-6411.
Bianco et al., "Acid Sphingomyelinase Activity Triggers Microparticle Release from Glial Cells", EMBO Journal, vol. 28, No. 8, 2009, pp. 1043-1054.
Bianco et al., "Astrocyte-Derived ATP Induces Vesicle Shedding and IL-1.Beta Release from Microglia", J. Immunol., vol. 174, No. 11, 2005, pp. 7268-7277.
Brennan et al., "Glioblastoma Subclasses can be defined by Activity among Signal Transduction Pathways and Associated Genomic Alterations", PloS One. vol. 4, No. 11, 2009, e7752.
Caby et al., "Exosomal-Like Vesicles are Present in Human Blood Plasma", International Immunology, vol. 17, No. 7, 2005, pp. 879-887.
Castellana et al., "Membrane Microvesicles as Actors in the Establishment of a favorable D Prostatic Tumoral Niche: A Role for Activated Fibroblasts and CX3CL1-CX3CR1 Axis", Cancer Res., vol. 69, 2009, pp. 785-793.
Castellana et al., "Membrane Microvesicles: Macromessengers in Cancer Disease and Progression", Thrombosis Research, vol. 125, Suppl. 2, 2010, S84-S88.
Chaput et al., "Exosome-Based Immunotherapy", Cancer Immunol Immunother, vol. 53, 2004, pp. 234-239.
Chen et al., "Microfluidic Isolation and Transcriptome Analysis of Serum Microvesicles", Lab Chip. 10, 2010, pp. 505-511.
Chin et al., "Changes in Serum Soluble VEGFR-1 and Tie-2 Receptors in Colorectal Cancer Patients Following Surgical Resections", Anticancer Research, vol. 24, 2004, pp. 2353-2358.
Choi et al., "Proteomic Analysis of Microvesicles Derived from Human Colorectal", J. Proteome. Res, vol. 6, 2007, pp. 4646-4655.
Cocucci et al., "Shedding Microvesicles: Artefacts no More", Trends in Cell Biology, vol. 19, No. 2, 2009, pp. 43-51.
Croce et al., "Molecular Origins of Cancer: Oncogenes and Cancer", New England Journal of Medicine, vol. 358, No. 5, Jan. 31, 2008, pp. 502-511.
D'Agostino et al., "Membrane Vesicles Shed by Oligodendroglioma Cells Induce Neurona Apoptosis", InterJ. Oncol, vol. 29, 2006, pp. 1075-1085.
Dean et al., "Proteomic and Functional Characterisation of Platelet Microparticle Size Classes", Thromb Haemost, vol. 102, 2009, pp. 711-718.
Del Conde et al., "Tissue-Factor-Bearing Microvesicles Arise From Lipid Rafts and Fuse with Activated Platelets to Initiate Coagulation", Blood, vol. 106, 2005, pp. 1604-1611.
Delves et al., "Prostasomes, Angiogenesis, and Tissue Factor", Semin. Thromb. Hemost, vol. 33, 2007, pp. 75-79.
Demuth et al., "Glioma Cells on the Run—The Migratory Transcriptome of 10 Human Glioma Cell Lines", BMC Genomics, vol. 9, No. 54, 2008, 1 page.
Denzel et al., "Initial Activation of EpCAM Cleavage via Cell-to-Cell Contact", BMC Cancer, vol. 9, No. 402, 2009, pp. 1-14.
Deregibus et al., "Endothelial Progenitor Cell Derived Microvesicles Activate an Angiogenic Program in Endothelial cells by a Horizontal Transfer of MRNA", Blood, vol. 110, 2007, pp. 2440-2448.
Di Vizio et al., "Oncosome Formation in Prostate Cancer: Association with a Region off Requent Chromosomal Deletion in Metastatic Disease", Cancer Res., vol. 69, 2009, pp. 5601-5609.

(56) References Cited

OTHER PUBLICATIONS

Dobrowolski et al., "Endocytic Control of Growth Factor Signalling: Multivesicular Bodies as Signalling Organelles", Nature Reviews|Molecular Cell Biology, vol. 13, Jan. 2012, pp. 53-60.
Dolo et al., "Matrix-Degrading Proteinases are Shed in Membrane Vesicles by Ovarian Cancer Cells in Vivo and in Vitro", Clin Exp Metastasis, vol. 17, No. 2, 1999, pp. 131-140.
Dolo et al., "Selective Localization of Matrix Metalloproteinase 9, Beta1 Integrins, and Human Lymphocyte Antigen Class I Molecules on Membrane Vesicles Shed by 8701-BC Breast", Cancer Res., vol. 58, 1998, pp. 4468-4474.
Dolo et al., "Shedding of Membrane Vesicles by Tumor and Endothelial Cells", Ital. J. Anat. Embryol., vol. 110, 2005, pp. 127-133.
Dvorak et al., "Tumor Shedding and Coaqulation", Science, vol. 212, 1981, pp. 923-924.
Ehnfors et al., "Horizontal Transfer of Tumor DNA to Endothelial Cells in Vivo", Cell Death. Differ. 16, 2009, pp. 749-757.
Extended European Search Report (includes Supplementary European Search Report and Search Opinion) received for European Patent Application No. 11768325.0, dated Aug. 14, 2013, 8 pages.
Extended European Search Report and Search Opinion received for European Patent Application No. 08783351.3, dated Sep. 30, 2010, 7 pages.
Extended European Search Report received for European Patent Application No. 13178357.3, dated Apr. 30, 2014, 9 pages.
Fevrier et al., "Exosomes: Endosomal-Derived Vesicles Shipping Extracellular Messages", Curro Opin. Cell Biol., vol. 16, 2004, pp. 415-421.
Final Office Action received for U.S. Appl. No. 12/673,528, dated Mar. 21, 2013, 15 pages.
Final Office Action received for U.S. Appl. No. 12/759,378, dated Mar. 1, 2013, 13 pages.
Flaumenhaft et al., "Megakaryocyte-Derived Microparticles: Direct Visualization and Distinction from Platelet-Derived Microparticles", Blood, vol. 113, No. 5, 2009, pp. 1112-1121.
Freije et al., "Gene Expression Profiling of Gliomas Strongly Predicts Survival", Cancer Research, vol. 64, 2004, pp. 6503-6510.
Friend et al., "Observations on Cell Lines Derived from a Patient with Hodgkin's Disease", Cancer Research, vol. 38, No. 8, 1978, pp. 2581-2591.
Gasser et al., "Activated Polymorphonuclear Neutrophils Disseminate Anti-Inflammatory Microparticles by Ectocvtosis", Blood, vol. 104, 2004, pp. 2543-2548.
Genderen et al., "Extracellular Annexin A5: Functions of Phosphatidylserine-Binding and Two-Dimensional Crystallization", Biochimica Et Blophvsica Acta, vol. 1783, 2008, pp. 953-963.
Gesierich et al., "Systemic Induction of the Angiogenesis Switch by the Tetraspanin D6.1A/CO-029", Cancer Res., vol. 66, 2006, pp. 7083-7094.
Ghosh et al., "Circulating Microvesicles in B-cell Chronic Lymphocytic Leukemia can Stimulate Marrow Stromal Cells: Implications for Disease Progression", Blood, vol. 115, No. 9, Mar. 4, 2010, pp. 1755-1764.
Giesen et al., "Blood-Borne Tissue Factor: Another View of Thrombosis", Proc. Natl. Acad. Sci. U.S.A., vol. 96, 1999, pp. 2311-2315.
Ginestra et al., "Membrane Vesicles in Ovarian Cancer Fluids: A New Potential Marker", Anticancer Research, vol. 19, No. 4C, 1999, pp. 3439-3445.
Ginestra et al., "The Amount and Proteolytic Content of Vesicles Shed by Human Cancel Cell Lines Correlates with theor in Vitro Invasiveness", Anticancer Research, vol. 18, No. 5(A), 1998, pp. 3433-3437.
Graner et al., "Proteomic and Immunologic Analyses of Brain Tumor Exosomes", FASEB J., vol. 23, 2009, pp. 1541-1557.
Graner et al., "The Heat Shock Response and Chaperones/Heat Shock Proteins in Brain Tumors: Surface Expression, Release, and Possible Immune Consequences", J. Neurosci, vol. 27, No. 42, 2007, pp. 11214-11227.

Guescini et al., "Astrocytes and Glioblastoma Cells Release Exosomes Carrying mtDNA", J. Neural Transm, vol. 117, No. 1, 2001, pp. 1-4.
Hao et al., "Epigenetic Transfer of Metastatic Activity by Uptake of Highly Metastatic B16 Melanoma Cell-Released Exosomes", Exp. Oncol. vol. 28, 2006, pp. 126-131.
Hegmans et al., "Proteomic Analysis of Exosomes Secreted by Human Mesothelioma Cells", American Journal of Patholoqy, vol. 164, No. 5, 2004, pp. 1807-1815.
Heijnen et al., "Activated Platelets Release Two Types of Membrane Vesicles: Microvesicles by Surface Shedding and Exosomes Derived From Exocytosis of Multivesicular Bodies and a-Granules", Blood, vol. 94, No. 11, 1999, pp. 3791-3799.
Helley et al., "Platelet Microparticles: A Potential Predictive Factor of Survival in Hormone-Refractory Prostate Cancer Patients Treated with Docetaxel-Based Chemotherapy", European Uroloqy, vol. 56, 2009, pp. 479-485.
Hoelzinger et al., "Gene Expression Profile of Glioblastoma Multiforme Invasive Phenotype Points to New Therapeutic Targets", Neoplasia, vol. 7, No. 1, 2005, pp. 7-16.
Holmgren et al., "Horizontal Transfer of DNA by the Uptake of Apoptotic Bodies", Blood, vol. 93, 1999, pp. 3956-3963.
Hong et al., "Colorectal Cancer Cell-Derived Microvesicles are Enriched in Cell Cycle- Related mRNAs that Promote Proliferation of Endothelial Cells", BMC. Genomics. vol. 10, 2009, p. 556.
Hood et al., "Paracrine Induction of Endothelium by Tumor Exosomes", Lab Invest., vol. 89, 2009, pp. 1317-1328.
Horstman et al., "Platelet Microparticles: A Wide-Angle Perspective", Critical Reviews in Oncology: Homatology, vol. 30, 1999, pp. 111-142.
Hotary et al., "Membrane Type I Matrix Metalloproteinase Usurps Tumor Growth Control Imposed by the Three- Dimensional Extracellular Matrix", Cell, vol. 114, 2003, pp. 33-45.
Hsu et al., "Getting Active: Protein Sorting in Edocytic Recyling", Nature Reviews|Molecular Cell Biology, 2012, pp. 1-6.
Huber et al., "Human Colorectal Cancer Cells Induce T-Cell Death Through Release of Oroaoootic Microvesicles: Role in Immune Escape", Gastroenterology, vol. 128, 2005, pp. 1796-1804.
Hudelist et al., "Her-2/Neu-Triggered Intracellular Tyrosine Kinase Activation: in Vivo Relevance of Ligand-Independent Activation Mechanisms and Impact upon the Efficacy of Trastuzumab-based Treatment", British Journal of Cancer, vol. 89, 2003, pp. 983-991.
Hugel et al., "Membrane Microparticles: Two Sides of the Coin", Physiology, vol. 20, 2005, pp. 22-27.
Huttner et al., "The Stem Cell Marker Prominin-1/CD133 on Membrane Particles in Human Cerebrospinal Fluid Offers Novel Approaches for Studying Central Nervous System Disease", Stem Cell, vol. 26, No. 3, 2008, pp. 698-705.
Iero et al., "Tumour-Released Exosomes and Their Implications in Cancer Immunity", Cell Death. Differ., vol. 15, 2008, pp. 80-88.
International Preliminary Report on Patentability received for PCT Patent Application No. PCT/CA2008/001441, dated Feb. 16, 2010, 6 pages.
International Preliminary Report on Patentability received for PCT Patent Application No. PCT/CA2011/000423, dated Oct. 26, 2012, 9 pages.
International Search Report received for PCT Patent Application No. PCT/CA2011/000423, dated Aug. 3, 2011, 6 pages.
International Search Report & Written Opinion received for PCT Patent Application No. PCT/CA2008/001441, dated Oct. 29, 2008, 7 pages.
Invitation to Pay Additional Fees received for PCT Patent Application No. PCT/CA2011/000423, dated Jun. 8, 2011, 2 pages.
Janowska-Wieczorek et al., "Microvesicles Derived from Activated Platelets Induce Metastasis and Anqioqenesis in Lunq Cancer", Int J Cancer, vol. 20, No. 113, 2005, pp. 752-760.
Johnstone, R. M.., "Exosomes Biological Significance: A Concise Review", Blood Cells Mol. Dis., vol. 36, 2006, pp. 315-321.
Jung et al., "CD44v6 Dependence of Premetastatic Niche Preparation by Exosomes", Neoplasia, vol. 11, 2009, pp. 1093-1105.
Kang et al., "Proteomic Analysis of Exosomes from Human Neural Stem Cells by Flow Field-Flow Fractionation and Nanoflow Liquid Chromatography-Tandem Mass Spectrometry", Journal of Proteome Research, vol. 7, 2008, pp. 3475-3480.

(56) References Cited

OTHER PUBLICATIONS

Keller et al., "Exosomes: From Biogenesis and Secretion to Biological Function", Immunology Letters, vol. 107, 2006, pp. 102-108.
Khalil et al., "Biomarker Discovery: A Proteomic Approach for Brain Cancer Profiling", Cancer Science, vol. 98, No. 2, Feb. 2007, pp. 201-213.
Kim et al., "Elevated Levels of Circulating Platelet Microparticles, VEGF, IL-6 and RANTES in Patients with Gastric Cancer: Possible Role of a Metastasis Predictor", Eur J. Cancer., vol. 39, No. 1, 2003, pp. 184-191.
Kim et al., "Extracellular Membrane Vesicles from Tumor Cells Promote Anqloqenosls via Sphlnqomvelin", Cancer Res., vol. 62, 2002, pp. 6312-6317.
Kim et al., "Fas Ligand-Positive Membranous Vesicles Isolated from Sera of Patients", Clin Cancer Res., vol. 11, 2005, pp. 1010-1020.
Koga et al., "Effect of Breast Cancer-Derived Secretory Vesicle Exosome Against Breast Cancer Cell Proliferation: Possibilities of Breast Cancer-Secretory Exosome as a Therapeutic Target", Japan Surgical Society Journal, vol. 106, 2005, p. 240.
Koga et al., "Purification, Characterization and Biological Significance of Tumor-Derived Exosomes", Anticancer Res., vol. 25, 2005, pp. 3703-3707.
Kumar et al., "Applications of Emerging Molecular Technologies in Glioblastoma Multiforme", Expert Rev Neurother, vol. 8, No. 10, 2008, pp. 1497-1506.
Lacroix et al., "Activation of Plasminogen into Plasmin at the Surface of Endothelial Microparticles: A Mechanism that Modulates Angiogenic Properties of Endothelial Progenitor Cells in Vitro", Blood, vol. 110, No. 7, 2007, pp. 2431-2439.
Lee et al., "Microvesicles as Mediators of Intercellular Communication in Cancer—The Emerging Science of Cellular 'Debris'", Seminars in Immunopathology, Jan. 13, 2011, pp. 455-467.
Lima et al., "Tumor-Derived Microvesicles Modulate the Establishment of Metastatic Melanoma in a Phosphatldylserine-Dependent Manner", Cancer Letters, vol. 283, 2009, pp. 168-175.
Liu et al., "Contribution of MyD88 to the Tumor Exosome- Mediated Induction of Myeloid Derived Suppressor Cells", Am. J. Pathol., vol. 176, No. 5, 2010, pp. 2490-2499.
Looze et al., "Proteomic Profiling of Human Plasma Exosomes Identifies PPARy as an Exosome-Associated Protein", Biochem Biophys Res. Commun, vol. 378, No. 3, 2009, pp. 433-438.
Mack et al., "Transfer of the Chemokine Receptor CCR5 between Cells by Membrane-Derived Microparticles: A Mechanism for Cellular Human Immunodeficiency Virus 1 Infection", Nat. Med, vol. 6, 2000, pp. 769-775.
Mathivanan et al., "Proteomics Analysis of A33 Immunoaffinity-Purified Exosomes released from the Human Colon Tumor Cell Line L1M1215 Reveals a Tissue-Specific Protein Signature", Mol. Cell Proteomics., vol. 9, 2010, pp. 197-208.
Mears et al., "Proteomic Analysis of Melanoma-Derived Exosomes by Two-Dimensional Polyacrylamide Gel Electrophoresis and Mass Spectrometry", Proteomics, vol. 4, No. 12, 2004, pp. 4019-4031.
Millimaggi et al., "Tumor Vesicle-Associated CD147 Modulates the Angiogenic Capablltv of Endothelial Cells", Neoplasia, vol. 9, 2007, pp. 349-357.
Muralidharan-Chari et al., "ARF6-Regulated Shedding of Tumor Cell-Derived Plasma Membrane Microvesicles", Curr Biol, vol. 19, 2009, pp. 1875-1885.
Muralidharan-Chari et al., "Microvesicles: Mediators of Extracellular Communication During Cancer Progression", J Cell Science, vol. 123, (Pt. 10), May 15, 2010, pp. 1603-1611.
Nomura et al., "Function and Role of Microparticles in Various Clinical Settings", Thrombosis Research, vol. 123, 2008, pp. 8-23.
Non Final Office Action received for U.S. Appl. No. 12/759,378, dated Jul. 10, 2014, 15 pages.
Non Final Office Action received for U.S. Appl. No. 12/673,528, dated Sep. 10, 2012, 34 pages.
Non Final Office Action received for U.S. Appl. No. 12/759,378 dated Aug. 2, 2012, 15 pages.
Non-Final Office Action received for U.S. Appl. No. 12/673,528, dated Sep. 24, 2014, 15 pages.
Notice of Allowance received for U.S. Appl. No. 12/673,528, dated Jul. 17, 2015, 8 pages.
Nutt et al., "Gene Expression-Based Classification of Malignant Gliomas Correlates Better with Survival than Histological Classification", Cancer Research, vol. 63, 2003, pp. 1602-1607.
Okamoto et al., "Expression of Constitutively Activated EGFRvIII in Non-Small Cell Lung Cancer", Cancer Sci., vol. 94, No. 1, Jan. 2003, pp. 50-56.
Olver et al., "Proteomic Analysis of Secreted Exosomes", Subcellular Biochemistry, vol. 43, 2007, pp. 99-131.
Park et al., "Hypoxia Modulates Tumor Microenvironment to Enhance Angiogenic and Metastastic Potential by Secretion of Proteins and Exosomes", Mol. Cell Proteomics, vol. 9, No. 6, 2010, pp. 1085-1099.
Partial European Search Report received for European Patent Application No. 13178357.3, dated Jan. 14, 2014, 7 pages.
Phillips et al., "Molecular Subclasses of High-Grade Glioma Predict Prognosis, Delineate a Pattern of Disease Progression, and Resemble Stages in Neurogenesis", Cancer Cell, vol. 9, 2006, pp. 157-173.
Piccin et al., "Circulating Microparticles: Pathophysiology and Clinical Implications", Blood Rev., vol. 21, No. 3, May 2007; Epub Nov. 24, 2006, pp. 157-171.
Pilzer et al., "Emission of Membrane Vesicles: Roles in Complement Resistance, Immunity and Cancer,", Springer Semin. Immunopathol., vol. 27, 2005, pp. 375-387.
Potolicchip et al., "Proteomic Analysis of Microglia-Derived Exosomes: Metabolic Role of the Aminopeptidase CD13 in Neuropeptide Catabolism", J Immunol, vol. 175, 2005, pp. 2237-2243.
Rabinowits et al., "Exosomal MicroRNA: A Diagnostic Marker for Lung Cancer", Clinical Lung Cancer, vol. 10, No. 1, 2009, pp. 42-46.
Ratajczak et al., "Embryonic Stem Cell-Derived Microvesicles Reprogram Hematopoietic Progenitors: Evidence for Horizontal Transfer of mRNA and Protein Elivery", Leukemia, vol. 20, 2006, pp. 847-856.
Ratajczak et al., "Membrane-Derived Microvesicles: Important and Underappreciated Mediators of Cell-to-Cell Communication", Leukemia, vol. 20, 2006, pp. 1487-1495.
Rauch et al., "Tissue Factor-Positive Microparticles in Blood Associated with Coaculooathv in Cancer", Thromb. Haemost., vol. 97, 2007, pp. 9-10.
Restriction Requirement for U.S. Appl. No. 12/673,528, dated Feb. 22, 2012, 10 pages.
Restriction Requirement received for for U.S. Appl. No. 13/641,085 dated Jun. 6, 2014, 7 pages.
Rich et al., "Gene Expression Profiling and Genetic Markers in Glioblastoma Survival", Cancer Res, vol. 65, No. 10, 2005, pp. 4051-4058.
Runz et al., "Malignant ascites-Derived Exosomes of Ovarian Carcinoma Patients Contain CD24 and EpCAM", Gynecol Oncol, vol. 107, No. 3, Dec. 2007; Epub Sep. 27, 2007, pp. 563-571.
Sanderson et al., "Generation of Novel, Secreted Epidermal Growth Factor Receptor (EGFR/ErbB 1) Isoforms via Metalloprotease-Dependent Ectodomain Shedding and Exosome Secretion", J. Cell Biochem., vol. 103, 2008, pp. 1783-1797.
Schiera et al., "Neurons Produce FGF2 and VEGF and Secrete them at Least in Part by Sheddinq Extracellular Vesicles", J. Cell Mol. Med., vol. 11, 2007, pp. 1384-1394.
Schorey et al., "Exosome Function: From Tumor Immunology to Pathogen Biology", Traffic, vol. 9., 2008, pp. 871-881.
Schwartz et al., "Proteomic-Based Prognosis of Brain Tumor Patients Using Direct- Tissue Matrix-Assisted Laser Desorption Ionization Mass Spectrometry", Cancer Research, vol. 65, No. 17, 2005, pp. 7674-7681.
Shet et al., "Characterizing Blood Microparticles: Technical Aspects and Challenges", Vascular Health and Risk Management, vol. 4, No. 4, 2008, pp. 769-774.

(56) References Cited

OTHER PUBLICATIONS

Sidhu et al., "The Microvesicle as a Vehicle for EMMPRIN in Tumor-Stromal Interactions", Oncogene, vol. 23, 2004, pp. 956-963.
Simak et al., "Cell Membrane Microparticles in Blood and Blood Products: Potentially Pathoqenic Agents and Diaqnostic Markers", Transfus. Med. Rev., vol. 20, 2006, pp. 1-26.
Simons et al., "Exosomes—Vesicular Carriers for Intercellular Communication", Curr. Opin. Cell Biol., vol. 21, 2009, pp. 575-581.
Simpson et al., "Exosomes: Proteomic Insights and Diagnostic Potential", Expert. Rev. Proteomics., vol. 6, 2009, pp. 267-283.
Simpson et al., "Proteomic Profiling of Exosomes: Current Perspectives", Proteomics, vol. 8, 2008, pp. 4083-4099.
Skinner et al., "Cellular Microvesicle Pathways Can Be Targeted to Transfer Genetic Information between Non-Immune Cells", PLoS One, vol. 4, No. 7, 2009, p. e6219.
Skog et al., "Glioblastoma Microvesicles Transport RNA and Proteins that Promote Tumour Growth and provide Diagnostic Biomarkers", Nat. Cell Biol., vol. 10, 2008, pp. 1470-1476.
Smalheiser, N. R., "Do Neural Cells Communicate with Endothelial Cells via Secretory Exosomes and Microvesicles?", Cardiovasc, Psychiatry Neurol., 2009, pp. 383-386.
Smalley et al., "Proteomic Discovery of 21 Proteins Expressed in Human Plasma-Derivedbut not Platelet-Derived Microparticles", Thromb Haemost., vol. 97, No. 1, 2007, pp. 67-80.
Somasundaram et al., "Serum Proteomics of Glioma: Methods and Applications", Expert Rev. Mol. Diagn., vol. 9, No. 7, 2009, pp. 695-707.
Taraboletti et al., "Bioavailability of VEGF in Tumor-Shed Vesicles Depends on Vesicleburst Induced by Acidic pH", Neoplasia, vol. 8,, 2006, pp. 96-103.
Taylor et al., "Isolation of Plasma Membrane Fragments From Cultured Murine Melanoma Cells", Biochem Biophys Res, Commun. vol. 113, No. 2, 1983, pp. 470-476.
Taylor et al., "Pregnancy-Associated Exosomes and their Modulation of T cell Signaling", Journal of Immunology, vol. 176, No. 3, Feb. 1, 2006, pp. 1534-1542.
Taylor et al., "Shed Membrane Fragment-Associated Markers for Endometrial and Ovarian Cancers", Gynecol Oncol, vol. 84, 2002, pp. 443-448.
Taylor et al., "Shedding of Plasma Membrane Fragments: Neoplastic and Developmental Importance", Chapter 3 in Developmental Biology vol. 3, 1986, pp. 33-57.
Taylor et al., "Tumour-Derived Exosomes and their Role in Cancer-Associated T-Cell Signaling Defects,", British Journal of Cancer, vol. 92, No. 2, Jan. 31, 2005, pp. 305-311.
Thery et al., "Exosomes: Composition, Biogenesis and Function", Nature Reviews Immunoloqy, vol. 2, No. 8, 2002, pp. 569-579.
Utsugi et al., "Elevated Expression of Phosphatidylserine in the Outer Membrane Leaflet of Human Tumor Cells and Recognition by Activated Human Blood Monocytes", Cancer Research, vol. 51, No. 11, 1991, pp. 3062-3066.

Valadi et al., "Exosome-Mediated Transfer of mRNAs and microRNAs is a Novel Mechanism of Genetic Exchange Between Cells", Nature Cell Biology, vol. 9, No. 6, Jun. 2007; Epub May 7, 2007, pp. 654-659.
Valenti et al., "Human Tumor-Released Microvesicles Promote the Differentiation of Myeloid Cells with Transforming Growth Factor-beta-Mediated Suppressive Activity on T Lymphocytes", Cancer Res, vol. 66, No. 18, 2006, pp. 9290-9298.
Van Doortnaal et al., "Cell-Derived Microvesicles and Cancer", Neth J. Med., vol. 67, No. 7, 2009, pp. 266-273.
Wang et al., "Endosomal Signaling of Epidermal Growth Factor Receptor Stimulates Signal Transduction Pathways Leading to Cell Survival", Molecular and Cellular Biology, vol. 22, No. 20, Oct. 2002, pp. 7279-7290.
Wikstrand et al., "Cell Surface Localization and Density of the Tumor-associated Variant of the Epidermal Growth Factor Receptor, EGFRvIII1", Cancer Research, vol. 57, Sep. 15, 1997, pp. 4130-4140.
Williams et al., "The Emerging Shape of the ESCRT machinery", Nature Reviews, Molecular Cell Biology, vol. 8, May 2007, pp. 355-368.
Wolfers et al., "Tumor-Derived Exosomes are a Source of shared Tumor Rejection Antiaens for CTL Cross-Prlrning", Nat. Med., vol. 7, 2001, pp. 297-303.
Written Opinion received for PCT Patent Application No. PCT/CA2011/000423 dated Aug. 3, 2011, 7 pages.
Wu et al., "A Human Functional Protein Interaction Network and Its Application to Cancer Data Analysis", Genome Biology, vol. 11, R53, 2010, 23 pages.
Wubbolts et al., "Proteomic and Biochemical Analyses of Human B Cell-derived Exosomes: Potential Implications for Their Function and Multivesicular Body Formation", Journal of Bioloaical Chemistry, vol. 278, No. 13, 2003, pp. 10963-10972.
Wysoczynski et al., "Lung Cancer Secreted Microvesicles: Underappreciated Modulators of Microenvironment in Oxoandlno Tumors", Int. J. Cancer., vol. 125, 2009, pp. 1595-1603.
Yu et al., "Contribution of Host-Derived Tissue Factor to Tumor Neovascularization", Arterioscler. Thromb. Vasc Biol. vol. 28, 2008, pp. 1975-1981.
Yu et al., "Oncogenic Events Regulate Tissue Factor Expression in Colorectal Cancer Cells: Implications for Tumor Progression and Angiogenesis", Blood, vol. 105, 2005, pp. 1734-1741.
Yu et al., "The Regulation of Exosome Secretion: A Novel Function of the p53 Protein", Cancer Res., vol. 66, 2006, pp. 4795-4801.
Zhang et al., "A Systems Biology-Based Gene Expression Classifier of Glioblastoma Predicts Survival with Solid Tumors,", PLOS One, vol. 4, No. 7, 2009, p. e6274.
Zhang et al., "Identification of Differentially Expressed Proteins in Human Glioblastoma Cell Lines and Tumors", GLiA, vol. 42, 2003, pp. 194-208.
Zwicker et al., "Predictive Value of Tissue Factor Bearing Microparticles in Cancer Associated Thrombosis", Thrombosis Research, vol. 125, 2010, pp. S89-S91.

* cited by examiner

TUMOR CELL-DERIVED MICROVESICLES

CROSS REFERENCE TO RELATED APPLICATIONS

This application is a continuation of U.S. application No. 12/673,528, now Pat. No. 9,186,405, which is a national stage of International Application No. PCT/CA 2008/001441, filed Aug. 8, 2008, which claims the benefit of U.S. Provisional Application No. 60/935,505, filed Aug. 16, 2007, the disclosures of which are incorporated herein by reference in their entirety.

TECHNICAL FIELD

The present invention relates to a method for diagnosis and prognosis of cancer and for monitoring the progression of cancer and/or the therapeutic efficacy of an anti-cancer treatment in a sample of a subject by detecting oncogenic proteins in microvesicles.

BACKGROUND OF THE INVENTION

The transformation of a normal cell into a malignant cell results, among other things, in the uncontrolled proliferation of the progeny cells, which exhibit immature, undifferentiated morphology, exaggerated survival and proangiogenic properties and expression, overexpression or constitutive activation of oncogenes not normally expressed in this form by normal, mature cells.

Oncogenic mutations and resultant intrinsic perturbations in cellular signaling are viewed as causal events in cancer development. For example, aggressive growth of human brain tumors (gliomas) is often associated with over-expression and amplification of the epidermal growth factor receptor (EGFR) and its ligand-independent, truncated mutant known as EGFRvIII (Cavenee, 2002, Carcinogenesis, 23: 683-686). The persistent activation of this oncogenic receptor triggers abnormal expression of genes involved in cell proliferation, survival and angiogenesis.

Many genetic mutations are known which result in the activation of oncogenes and thereby increase the chance that a normal cell will develop into a tumor cell. In addition, inactivation of tumor suppressor genes, which function normally to counteract oncogenes by repairing DNA damage, or by inducing apoptosis of damaged cells, and keeping cellular activities under control, can also lead to cancer. There is much evidence to support the notion that activation of oncogenes or inactivation of tumor suppressors can lead to cancer (Hanahan & Weinberg, 2000, Cell, 100: 57-70). Mutations of proto-oncogenes in somatic cells are increasingly recognized as significant in the initiation of human cancers. Some examples of oncogenes formed by such mutations include: neu, fes, fos, myc, myb, fms, Ha-ras, and Ki-ras. Much needs to be learned in order to understand how oncogenes and their expression products function to transform normal cells into cancer cells.

Growth factors and their receptors are involved in the regulation of cell proliferation and they also appear to play a key role in oncogenesis. For example, the following three proto-oncogenes are related to a growth factor or a growth factor receptor: 1) c-sis, which is homologous to the transforming gene of the simian sarcoma virus and is the B chain of platelet-derived growth factor (PDGF); 2) c-fms, which is homologous to the transforming gene of the feline sarcoma virus and is closely related to the macrophage colony-stimulating factor receptor (CSF-1R); and 3) c-erbB, which encodes the epidermal growth factor receptor (EGFR) and is homologous to the transforming gene of the avian erythroblastosis virus (v-erbB). The two receptor-related proto-oncogenes, c-fms and c-erbB, are members of the tyrosine-specific protein kinase family to which many proto-oncogenes belong.

In addition, aggressive growth of human brain tumors (gliomas) is often associated with over-expression and amplification of EGFR and its ligand-independent, truncated mutant known as EGFRvIII. The persistent activation of this oncogenic receptor triggers abnormal expression of genes involved in cell proliferation, survival and angiogenesis.

Several groups have investigated the expression of EGFR in a variety of tumors using quantitative as well as semi-quantitative immunohistochemical methods. The types of tumors investigated include gynecological, bladder, head and neck, lung, colorectal, pancreatic and breast carcinomas. Such studies almost exclusively rely upon radioligand binding methodology or immunorecognition for quantifying EGFR in tissue samples.

The most extensive correlations of EGFR expression with clinical data have been carried out in studies with breast cancer patients dating back several decades (e.g. Nicholson et al., 1988, Int. J. Cancer, 42: 36-41). In several studies with up to 246 patients, it was demonstrated that EGFR is a highly significant marker of poor prognosis for breast cancer. It is considered to be one of the most important variables in predicting relapse-free and overall survival in lymph node-negative patients, and to be the second most important variable, after nodal status, in lymph node-positive patients. In general, EGFR positive tumors are larger and occur in a higher proportion of patients with lymph node involvement. The prognostic significance of EGFR/ErbB1/HER-1 is enhanced by a simultaneous detection of its related and Interacting oncogenic receptor tyrosine kinase known as ErbB2/HER-2/neu, a target of herceptin (Citri & Yarden, 2006, Nature Rev. Mol. Cell. Biol., 7: 505-516).

Mutated oncogenes are therefore markers of malignant or premalignant conditions. It is also known that other, non-oncogenic portions of the genome may be altered in the neoplastic state. There is widespread recognition of the importance of tests for early detection of cancer. In some cases, abnormal or malignant cells exfoliated from the surface of an organ can be identified by cytologic examination of brushings and fluids. For example, a PAP smear (Papanicolaou test) may detect abnormal (e.g., pre-cancerous or cancerous) cells of the cervix. Alternatively, genetic abnormalities in cancer cells or pre-cancer cells may be detected using molecular techniques. For example, techniques such as DNA sequence or methylation analysis may be used to detect specific mutations and/or structural as well as epigenetic alterations in DNA.

Nucleic acid based assays can detect both oncogenic and non-oncogenic DNA, whether mutated or non-mutated, provided that cancer cells or their related cellular debris are directly available for analysis (e.g. in surgical or biopsy material, lavage, stool, or circulating cancer cells). In particular, nucleic acid amplification methods (for example, by polymerase chain reaction) allow the detection of small numbers of mutant molecules among a background of normal ones. While alternate means of detecting small numbers of tumor cells (such as flow cytometry) have generally been limited to hematological malignancies, nucleic acid amplification assays have proven both sensitive and specific in identifying malignant cells and for predicting prognosis following chemotherapy (Fey et al., 1991. Eur. J. Cancer 27: 89-94).

Various nucleic acid amplification strategies for detecting small numbers of mutant molecules in solid tumor tissue have been developed, particularly for the ras oncogene (Chen and Viola, 1991, Anal. Biochem. 195: 51-56). For example, one sensitive and specific method identifies mutant ras oncogene DNA on the basis of failure to cleave a restriction site at the crucial 12th codon (Kahn et al., 1991, Oncogene, 6: 1079-1083). Similar protocols can be applied to detect any mutated region of DNA in a neoplasm, allowing detection of other oncogene-containing DNA or tumor-associated DNA.

Many studies use nucleic acid amplification assays to analyze the peripheral blood of patients with cancer in order to detect intracellular DNA extracted from circulating cancer cells, including one study which detected the intracellular ras oncogene from circulating pancreatic cancer cells (Tada et al., 1993, Cancer Res. 53: 2472-4). The assay is performed on the cellular fraction of the blood, i.e. the cell pellet or cells within whole blood, and the serum or plasma fraction is ignored or discarded prior to analysis. Since such an approach requires the presence of metastatic circulating cancer cells (for non-hematologic tumors), it is of limited clinical use in patients with early cancers, and it is not useful in the detection of non-invasive neoplasms or pre-malignant states.

It has not been generally recognized that nucleic acid amplification assays can detect tumor-associated extracellular mutated DNA, including oncogene DNA, in the plasma or serum fraction of blood. Furthermore, it has not been recognized that this can be accomplished in a clinically useful manner, i.e. rapidly within one day, or within less than 8 hours.

Detection of a mutant oncogene by nucleic acid amplification assay, in peripheral blood plasma or serum, has been the subject of reports in the prior art. However, this method requires time-consuming and technically demanding approaches to DNA extraction and are thus of limited clinical utility.

Tests for proteins expressed by certain cancers may be performed. For example, screening for prostate-specific antigen (PSA) may be used to identify patients at risk for, or having prostate cancer. Still, PSA screening may suffer from variability of assay methods and a lack of specificity. For example, although malignant prostate cells make higher amounts of PSA, PSA is not specific to cancer cells but is made by both normal and cancerous prostate cells. PSA levels may vary depending upon the age of the patient, the physiology of the prostate, the grade of the cancer, and the sensitivity of PSA levels to pharmacologic agents. Also, the molecular basis for many cancers is as yet unknown, and therefore, molecular tests are not yet comprehensive enough to detect most cancers.

Thus, detection of many cancers still relies on detection of an abnormal mass in the organ of interest. In many cases, a tumor is often detected only after a malignancy is advanced and may have metastasized to other organs. For example, breast cancer is typically detected by obtaining a biopsy from a lump detected by a mammogram or by physical examination of the breast. Also, although measurement of prostate-specific antigen (PSA) has significantly improved the detection of prostate cancer, confirmation of prostate cancer typically requires detection of an abnormal morphology or texture of the prostate. Thus, there is a need for methods and devices for earlier detection of cancer. Such new methods could, for example, replace or complement the existing ones, reducing the margins of uncertainty and expanding the basis for medical decision making.

As indicated above, several methods have been used to detect EGFR levels in tumor tissues. There are, however, many cases in which tissue is not readily available or in which it is not desirable or not possible to withdraw tissue from tumors. Therefore, there is a need in the medical art for rapid, accurate diagnostic tests that are convenient and non-traumatic to patients.

Thus, it would be highly desirable to be provided with a method that permits medically useful, rapid, and sensitive detection of mutated oncogenes associated with cancer.

SUMMARY OF THE INVENTION

The present invention relates to a method for diagnosing or determining prognosis of a cancer in a subject, comprising the steps of collecting a sample from the subject, isolating microvesicles from the sample and detecting the presence of an oncogenic protein in the microvesicles, wherein the presence of the oncogenic protein in the sample is indicative that the subject may have cancer.

There is also provided in accordance with the present invention a method of detecting the presence of an oncogenic protein in a subject, comprising collecting a sample from the subject, isolating microvesicles from the sample, and detecting the presence of the oncogenic protein in the microvesicles.

Furthermore, the method disclosed herein can further comprise the step of measuring the phosphorylation state of the oncogenic protein.

In accordance with the present invention, there is also disclosed a kit for detecting a cancer in a sample from a subject comprising at least one antibody against an oncogenic protein, and instructions for using said at least one antibody to detect the oncogenic protein in microvesicles in the sample.

In accordance with the present invention, there is also provided a use of at least one antibody for diagnosing or determining prognosis of a cancer in a sample of a subject, wherein said at least one antibody binds to an oncogenic protein present in microvesicles.

In a particular embodiment, the at least one antibody is a phosphospecific antibody.

There is also disclosed herein a use of an agent blocking exchange of microvesicles for treating cancer. In a particular embodiment, the agent is annexin V or a derivative thereof or an agent blocking P-selectin or its ligand PSGL.

In accordance with the present invention, there is also provided a method for monitoring progression of a cancer in a subject, comprising the steps of collecting a first sample from a subject having cancer at a first timepoint, isolating microvesicles from the first sample, and measuring an oncogenic protein in the microvesicles obtained from the first sample; and collecting a second sample from the subject having cancer at a second timepoint, the second timepoint occurring after the first timepoint, isolating microvesicles from the second sample, and measuring the oncogenic protein in the microvesicles obtained from the second sample, wherein a change in the amount of the oncogenic protein in the microvesicles obtained from the second sample compared to the amount of the oncogenic protein in the microvesicles obtained from the first sample is indicative of progression of the cancer.

It is also encompassed that the first timepoint may occur before the subject has received the anti-cancer treatment, and the second timepoint may occur after the subject has received the anti-cancer treatment. In another embodiment, both timepoints may occur after the subject has received the anti-cancer treatment.

In another embodiment, a reduction or no change in the amount of the oncogenic protein in the microvesicles obtained from the second sample compared to the amount of the oncogenic protein in the microvesicles obtained from the first sample indicates therapeutic efficacy of the anti-cancer treatment.

In accordance with the present invention, there is also provided a method for monitoring therapeutic efficacy of an anti-cancer treatment, comprising the steps of collecting a first sample from a subject having cancer at a first timepoint, isolating microvesicles from the first sample, and measuring an oncogenic protein in the microvesicles obtained from the first sample; and collecting a second sample from the subject having cancer at a second timepoint, the second timepoint occurring after the first timepoint, isolating microvesicles from the second sample, and measuring the oncogenic protein in the microvesicles obtained from the second sample; wherein a reduction or no change in the amount of the oncogenic protein in the microvesicles obtained from the second sample compared to the amount of the oncogenic protein in the microvesicles obtained from the first sample indicates therapeutic efficacy of the anti-cancer treatment.

In one embodiment, the first timepoint occurs before the subject has received the anti-cancer treatment, and the second timepoint occurs after the subject has received the anti-cancer treatment. Alternatively, the first and second timepoints may both occur after the subject has received the anti-cancer treatment. In yet another embodiment, the first and second timepoints may both occur in the absence of anti-cancer treatment, or before the subject receives anti-cancer treatment, and the amount of the oncogenic protein in microvesicles obtained from the second sample compared to that in the first sample would provide an indication of the progression or aggressiveness of the cancer.

In another embodiment, at least two oncogenic proteins are detected in the microvesicles. More specifically, the oncogenic proteins can be EGFR and HER-2, or HER-2 and HER-3, or EGFRvIII and HER-2.

In another embodiment, the microvesicles are isolated by ultracentrifugation, immunoprecipitation or microfiltration.

Furthermore, the presence of the oncogenic protein in the microvesicles can be detected or measured by immunoblot, immunoprecipitation, ELISA, RIA, flow cytometry, electron microscopy or mass spectrometry.

The methods as described herein can further comprise the step of measuring the phosphorylation state of the oncogenic protein in the microvesicles obtained from the first and second sample.

In another embodiment, a reduction or no change in phosphorylation of the oncogenic protein in the microvesicles obtained from the second sample compared to the amount of phosphorylation of the oncogenic protein in the microvesicles obtained from the first sample indicates therapeutic efficacy of the anti-cancer treatment.

Alternatively, an increase in phosphorylation of the oncogenic protein in the microvesicles obtained from the second sample compared to the amount of phosphorylation of the oncogenic protein in the microvesicles obtained from the first sample indicates that the cancer has progressed or continued to proliferate.

Furthermore, a reduction in phosphorylation of the oncogenic protein in the microvesicles obtained from the second sample compared to the amount of phosphorylation of the oncogenic protein in the microvesicles obtained from the first sample indicates that the cancer has regressed.

Further, no change in phosphorylation of the oncogenic protein in the microvesicles obtained from the second sample compared to the amount of phosphorylation of the oncogenic protein in the microvesicles obtained from the first sample indicates that the cancer has not progressed.

In accordance with the present invention, there is also provided an isolated microvesicle comprising an oncogenic protein.

In a particular embodiment, the anti-cancer treatment is surgery, radiology, chemotherapy, or a targeted cancer treatment. More specifically, the targeted cancer treatment is selected from the group consisting of small molecules, monoclonal antibodies, cancer vaccines, antisense, siRNA, aptamers and gene therapy.

In another embodiment, the encompassed cancer is selected from the group consisting of breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, gastrointestinal stromal tumors (GIST), fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, astrocytoma, glioblastoma multiforme, oligodendroglioma, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, pediatric glioma, medulloblastoma, Wilms tumor, osteosarcoma, teratoma, rhabdomyoblastoma and sarcoma.

In yet another embodiment, the oncogenic protein is selected from the group consisting of EGFRvIII, EGFR, HER-2, HER-3, HER-4, MET, cKit, PDGFR, Wnt, beta-catenin, K-ras, H-ras, N-ras, Raf, N-myc, c-myc, IGFR, PI3K, Akt, BRCA1, BRCA2, PTEN, and receptors of cells associated with cancer (cancer-related receptors) such as VEGFR-2, VEGFR-1, Tie-2, TEM-1 and CD276.

In addition, the sample is a bodily fluid, or more specifically, a body fluid selected from the group consisting of blood, urine, lymph, cerebrospinal fluid, ascites, saliva, lavage, semen, glandular secretions, exudate, contents of cysts and feces.

BRIEF DESCRIPTION OF THE DRAWINGS

Having thus generally described the nature of the invention, reference will now be made to the accompanying drawings, showing by way of illustration, an embodiment or embodiments thereof, and in which.

DETAILED DESCRIPTION OF THE PREFERRED EMBODIMENT

Figure 1:
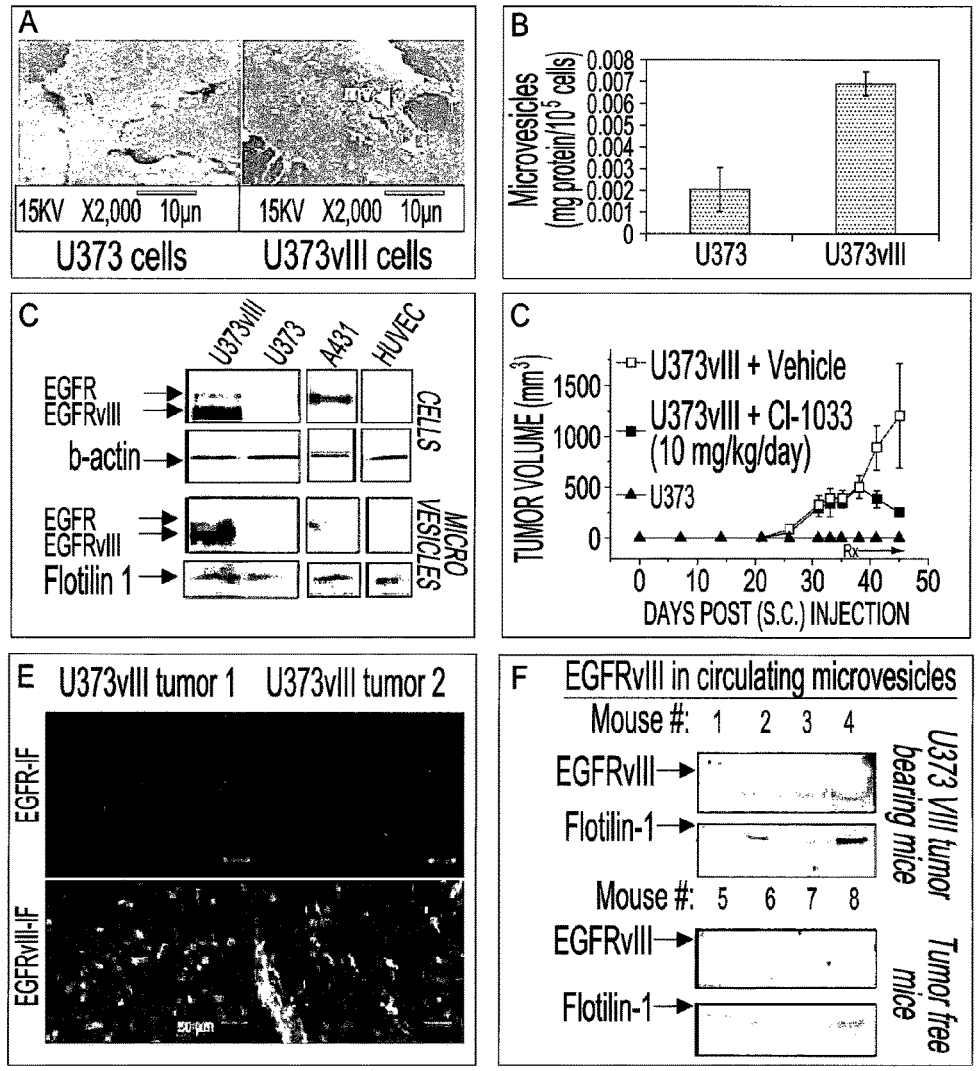
FIG. 1 illustrates the production of EGFRvIII-containing microvesicles by human glioma cells wherein in (A) the generation of multiple microvesicular structures on the surfaces of U373vIII glioma cells harboring EGFRvIII oncogene (white arrowheads; SEM image), but not by their indolent parental U373 counterparts, is shown; in (B) the increase in abundance of the microvesicular fraction of the conditioned media, as a function of EGFRvIII expression in U373 glioma (measured by total protein content) is shown; in (C) the inclusion of oncogenic EGFRs in lipid raft-derived microvesicles released by EGFR-expressing cancer cells is shown; in (D) the dependence of tumorigenic properties of U373vIII cells on functional EGFRvIII is shown; in (E) the predominant expression of EGFRvIII but not EGFR in U373vIII tumors is shown; in (F) the release of EGFRvIII containing and flotilin-1-positive microvesicles to the circulating blood of SCID mice harbouring U373vIII tumors (top panels) is shown.

In accordance with the present invention, there is provided a method of detecting the presence of an oncogenic protein in a subject, comprising collecting a sample from the subject, isolating microvesicles from the sample, and detecting the presence of the oncogenic protein in the microvesicles.

There is also provided herein a method for diagnosing cancer in a sample of a subject by detecting oncogenic proteins in microvesicles.

In an embodiment, cancer is detected by analyzing microvesicles in a sample, such as a bodily fluid, such as blood, urine, cerebrospinal fluid, lymph, ascites, saliva, lavage, semen, and glandular secretions, as well as feces, exudate, contents of cysts and other sources.

In another embodiment, a method for prognosis of cancer, by detecting oncogenic proteins in microvesicles, is provided.

In yet another embodiment, a method for monitoring progression of cancer and/or response to treatment is provided.

Cancer refers herein to a cluster of cancer cells showing over proliferation by non-coordination of the growth and proliferation of cells due to the loss of the differentiation ability of cells.

The term "cancer" includes but is not limited to, breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer (generally considered the same entity as colorectal and large intestinal cancer), fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma (also known as intraocular melanoma), testicular cancer, oral cancer, pharyngeal cancer or a combination thereof. In an embodiment, the cancer is a brain tumor, e.g. glioma. In another embodiment, the cancer expresses the HER-2 or the HER-3 oncoprotein. The term "cancer" also includes pediatric cancers, including pediatric neoplasms, including leukemia, neuroblastoma, retinoblastoma, glioma, rhabdomyoblastoma, sarcoma and other malignancies.

Non-limiting examples of oncogenic proteins which can be detected using the methods of the invention are as follows: (i) membrane-associated oncoproteins derived from cancer cells such as EGFRvIII in glioma, EGFR in squamous cell carcinoma, glioma, lung cancer, or bladder cancer, breast cancer mutant (e.g. Iressa sensitive, mutant or non-expressed tumor suppressor proteins BRCA1 and/or BRCA2), EGFR in lung cancer, HER-2 in breast and ovarian carcinoma, MET in various metastatic and invasive cancers, Kit in gastro-intestinal stromal tumors, PDGFR in glioma, Wnt in various tumors, various phosphatases; (ii) combinatorial clusters of transforming receptors such as EGFR/HER-2 in breast cancer, HER-2/HER-3 in various tumors; (iii) membrane-associated cytoplasmatic molecules with transforming properties such as K-ras in colorectal, pancreatic and lung cancer, PTEN (lack of) in glioma and prostate cancer, (iv) signaling complexes that could be present (and active) in lipid rafts and microvesicles such as PI3K/Akt, Raf/MEK/MAPK; and (v) tumor related endothelial receptor related to tumor angiogenesis and antiangiogenesis such as VEGFR-2, VEGFR-1, Tie-2 and TEMs (e.g. TEM-1, CD276). These proteins may be detected alone or in combination.

Other non-limiting examples of oncogenic proteins include EGFRvIII, EGFR, HER-2, HER-3, HER-4, MET, cKit, PDGFR, Wnt, beta-catenin. K-ras, H-ras, N-ras, Raf, N-myc, c-myc, IGFR, IGFR, PI3K, and Akt; tumor suppressor proteins such as BRCA1, BRCA2 and PTEN; cancer-related host receptors and microvesicle-associated molecules, e.g. those involved in angiogenesis such as VEGFR-2, VEGFR-1, Tie-2, TEM-1 and CD276. It is contemplated that all oncogenic proteins, tumor suppressor proteins, host-cell related receptors and microvesicle-associated molecules may be used, alone or in combination, in the methods, compositions and kits of the present invention. It is further contemplated that any oncogenic protein, and any combination of oncogenic proteins, which is determined to be mechanistically, diagnostically, prognostically or therapeutically important for cancer, may be used in the methods, compositions and kits of the present invention.

The invention described herein is based, at least in part, on the novel and unexpected observation that EGFRvIII oncoprotein can be emitted and shared between glioma cells via intercellular transfer of the activated receptor that occurs as cargo of membrane-derived microvesicles released from cells producing the mutant protein. Indeed, EGFRvIII stimulates the formation of lipid-raft related microvesicles, to which it becomes incorporated.

Microvesicles containing EGFRvIII oncoprotein are released to conditioned media or blood of tumor bearing mice and can merge with the plasma membranes of tumor cells lacking this receptor. Such transfer of EGFRvIII triggers the activation of downstream signaling pathways (MAPK and Akt), progression-related changes in gene expression (VEGF, BclxL, p27) and manifestation of exacerbated cellular transformation, notably altered morphology and increased soft agar colony formation efficiency. These observations point to the role of membrane microvesicles in horizontal propagation of transforming proteins between different subsets of cancer cells and suggest that the transforming impact of membrane-associated oncoproteins may extend beyond the cells harboring the corresponding mutant genes.

Activated cells of various types are known to produce and shed into their surroundings membrane microvesicles, also known as microparticles, ectosomes, or argosomes; in the case where such vesicles originate from the lysosomal pathway, they are often referred to as exosomes. The biological role of these structures is poorly understood, but may include secretory processes, immunomodulation, coagulation and intercellular communication (Janowska-Wieczorek et al., 2005, Int. J Cancer, 20: 752-760).

Microvesicles may vary in the mechanism of their generation, size and composition, but often (especially ectosomes) contain material associated with membrane lipid rafts, including functional transmembrane proteins. For instance, procoagulant tissue factor (TF) can be released in this fashion from inflammatory cells and, importantly, becomes subsequently incorporated into membranes of platelets, endothelium and other cells where it exerts its biological effects. As used herein, the term "microvesicles" includes microvesicles, microparticles, ectosomes, argosomes, exosomes, tumor vesicles and all other vesicular bodies released from cells.

Cancer cells lacking the p53 tumor suppressor gene may in some instances mimic this process by releasing altered amounts of TF-containing (Yu et al., 2005, Blood, 105: 1734-1741), or secretory (Yu et al., 2006, Cancer Res, 66: 4795-47801) microvesicles to blood and the pericellular milieu.

Oncogenic receptors often reside within the regions of the plasma membrane, from which microvesicles originate in cancer cells (e.g. lipid rafts). It is disclosed herein that the oncogenic receptors can themselves become included in the microvesicle cargo. This is of particular interest for example in malignant brain tumors (gliomas) where activation of membrane associated EGFR represents a major transforming event, and in nearly 30% of cases with glioblastoma multiforme (GBM) expression of the EGFRvIII oncogenic mutant is readily detectable.

In order to explore this phenomenon further, the production of microvesicles by cultured U373 glioma cells lacking the activated EGFR and their counterparts, engineered to express EGFRvIII (U373vIII cells) was examined. Interestingly, the presence of the EGFRvIII oncogene in the latter cell line resulted in formation of multiple vesicular protrusions on the cell surface, an effect that was accompanied by an increase in recovery of protein from the microvesicular fraction of the culture media (see FIG. 1A, B). This material contained a proportional quantity of flotilin-1, a protein associated with membrane lipid rafts and often found in raft-related microvesicles from various sources. Collectively, it demonstrates that EGFRvIII-related transformation observed in U373vIII cells is coupled with increased production of microvesicles derived from membrane lipid rafts.

In a particular embodiment, proteins enriched in microvesicles, such as EGFRvIII. HER-2, and MET, can be detected by various techniques known in the art. For example, lysates of microvesicles can be analyzed by immunoblotting using antibodies such as anti-EGFRvIII or anti-EGFR. Concentration of the microvesicles by centrifugation is necessary, but also provides a considerable quantitative and qualitative advantage over the analysis of the whole plasma. This is because microvesicle isolation can improve the sensitivity of detection of certain molecules, e.g. EGFRvIII (due to their enrichment in microvesicles), increase the specificity (as microvesicles are not random collections of plasma membrane molecules) and broaden the scope of the analysis (owing to the presence of unique and diagnostically informative combinations of proteins in microvesicle cargo). In this regard, the sensitivity of microvesicle analysis can be increased by switching from ultracentrifugation to microfiltration, the latter of which may simplify and improve the recovery of microvesicles. Another technique to detect microvesicular proteins is immunoprecipitation of microvesicle-related material from magnetic beads coated with e.g. Annexin V or an antibody binding an oncogenic protein, such as anti-EGFRvIII antibody. Further, an ELISA assay based on two antibodies (e.g. 2×anti-EGFRvIII or anti- EGFRvIII+anti-EGFR) or a radioimmune assay (RIA) based on two antibodies (e.g. 2×anti-EGFRvIII or anti-EGFRvIII+anti-EGFR) can also be used. In addition, ELISA based on binding of microvesicles to surfaces coated with Annexin V (as e.g. in commercial TF assays) or with EGFRvIII/EGFR antibodies could be used in conjunction with a detection component based on the anti-EGFRvIII antibody. Other techniques that can be used include flow cytometry, where microvesicles are captured by beads coated with e.g. Annexin V and stained with e.g. anti-EGFRvIII antibody, and mass spectrometry, where EGFR is detected in the proteome of microvesicle preparations. It is contemplated that standard techniques known in the art for preparation of microvesicles and for detection of proteins can be used in the methods described herein.

The present invention is based, at least in part, on the observation that abundant expression of EGFRvIII protein is detected in lysates not only of U373vIII cells themselves, but also in their derived microvesicles, demonstrating that the intact oncoprotein is released in this fashion to the extracellular space. Although the parental U373 cells did release detectable quantities of flotilin-1 containing microvesicles, they contained only trace amounts of wild type EGFR (wtEGFR) and no EGFRvIII. These results were validated against EGFR-negative endothelial cells (HU-VEC) and A431 cells expressing only wtEGFR, as well as their respective microvesicle preparations (FIG. 1C). While U373 cells exhibit indolent phenotype in vivo, their U373vIII counterparts readily form subcutaneous tumors in immunodeficient (SCID) mice, in a manner susceptible to inhibition by daily doses of an irreversible, small molecule pan-Erb inhibitor CI-1033 (FIG. 1D). U373vIII tumors stained strongly for EGFRvIII but not for wtEGFR and, interestingly, emitted EGFRvIII-containing microvesicles into the systemic circulation (FIG. 1E, F). Thus, expression of mutant EGFRvIII gene leads to the increased aggressiveness of glioma cells coupled with extracellular release of microvesicles containing an intact EGFRvIII oncoprotein.

Heterogenous EGFRvIII expression in human glioma suggests that different tumor cell subsets could shed EGFRvIII-containing microvesicles into the common intercellular space. Since microvesicles can readily fuse with cellular membranes via a phosphatidylserine-dependent mechanism, it is here demonstrated that oncogenic EGFRvIII can be transferred in this manner from more aggressive to indolent glioma cells. EGFRvIII-negative U373 cells were, therefore, incubated with preparations of microvesicles obtained from either their U373vIII counterparts harboring EGFRvIII, or from U373vIII-GFP cells engineered to express a green fluorescent protein (GFP)-tagged EGFRvIII oncogene (EGFRvIII-GFP). Interestingly, this resulted in an extensive uptake of the microvesicular content by U373 cell, as demonstrated by their de novo surface expression of the EGFRvIII antigen and GFP fluorescence, respectively (FIG. 2A-D).

Figure 3:
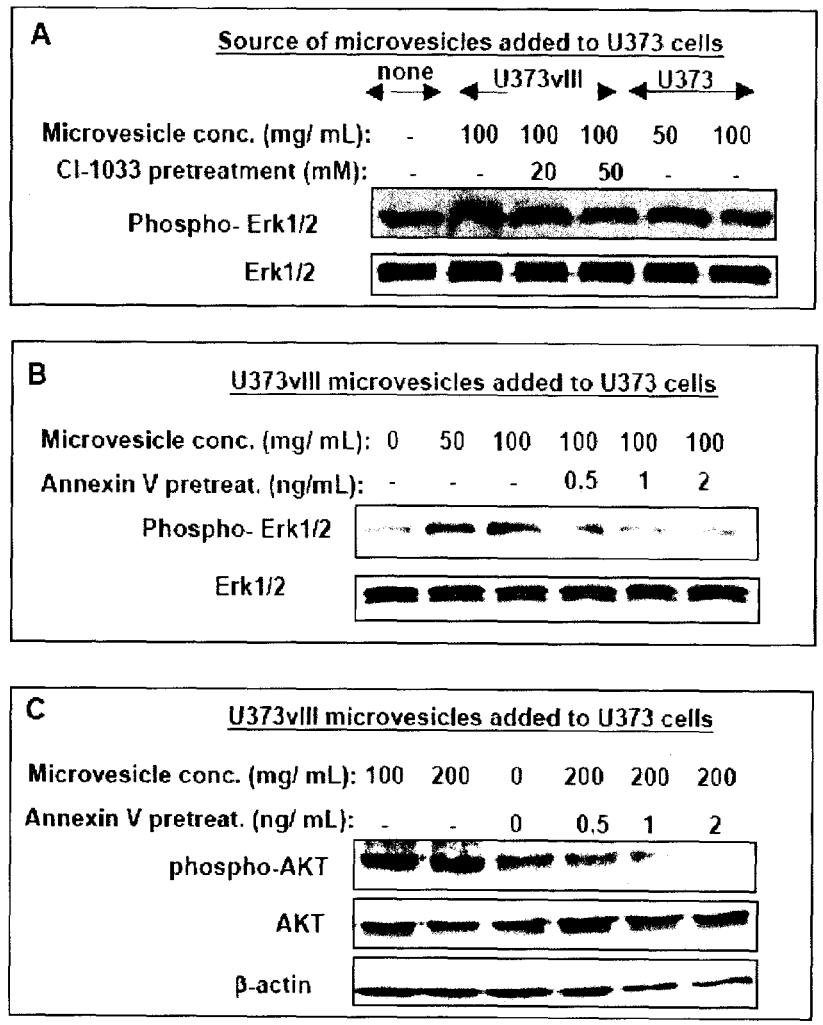
FIG. 3 illustrates the activation of growth promoting signaling pathways in cells that have acquired oncogenic EGFRvIII through microvesicle-mediated intercellular transfer, wherein in (A) it is shown the EGFRvIII-dependent increase in Erk1/2 phosphorylation in U373 cells that have incorporated microvesicles shed by U373vIII cells; in (B) Inhibition of Erk1/2 phosphorylation in U373 cells by blocking their uptake of EGFRvIII-containing microvesicles with annexin V is observed; and in (C) the increase in phosphorylation of Akt in U373 cells that have incorporated EGFRvIII-containing microvesicles is observed.

The apparent intercellular microvesicle-mediated transfer of the ostensibly intact EGFRvIII receptor raises the question, as to the signaling consequences (if any) of this event for the 'acceptor' (U373) cells. To address this question, U373 cells 24 hours after their exposure to EGFRvIII-containing microvesicles were examined for activation of the MAPK and Akt cascades, both known to mediate transforming effects downstream of this oncogene. Indeed, incorporation of EGFRvIII into the U373 plasma membrane resulted in a consistent increase in Erk1/2 phosphorylation. This event was dependent on the transfer of active EGFRvIII, as U373-derived microvesicles, containing no EGFRvIII were ineffective. Moreover, the irreversible blockade of this receptor by preincubation of U373vIII-derived microvesicles with pan-ErbB inhibitor (CI-1033) markedly reduced Erk1/2 phosphorylation (FIG. 3A). Phosphorylation of Erk1/2 was also abrogated by preincubation of these microvesicles with annexin V, which blocks their exposed phosphatidylserine residues and thereby their uptake by U373 cells. These results demonstrate that not just mere contact between the EGFRvIII containing microvesicles with the surface of U373 cells, but rather their actual (phosphatidylserine-dependent) integration and EGFRvIII transfer are required for triggering the activation of MAPK pathway in the acceptor cells (FIG. 3B). Incorporation of U373vIII-derived microvesicles also induced phosphorylation of Akt in U373 cells, in a manner inhibitable by annexin V (FIG. 3C), and triggered several other events, notably phosphorylation of PDK1 and Raf.

The transforming effects of EGFRvIII-dependent pathways are ultimately mediated by deregulation of several genes responsible for tumor growth, survival and angiogenesis. With regard to the latter, it was noted that U373 cells exposed to U373vIII-derived microvesicles exhibited a marked (2-3 fold) increase in production of vascular endothelial growth factor (VEGF), a potent mediator of brain tumor angiogenesis and a known EGFR target. EGFRvIII activity was essential for this effect as U373-derived microvesicles (devoid of EGFRvIII), or those from U373vIII, but preincubated with CI-1033 were unable to induce this release of VEGF (FIG. 4A). In these settings, EGFRvIII containing microvesicles also robustly stimulated VEGF promoter activity and this effect was abrogated by their pretreatment with annexin V (FIG. 4B). Collectively, these observations demonstrate that incorporation of U373vIII microvesicles triggers an EGFRvIII-dependent increase in VEGF gene expression and protein production by U373 cells, via activation of the MAPK and Akt pathways.

While VEGF upregulation often heralds activation of oncogenic pathways, cellular transformation downstream of EGFRvIII is mediated by changes in expression of genes directly involved in cellular proliferation and survival. In this regard, U373 cells treated with EGFRvIII-containing microvesicles revealed an increase in expression of the antiapoptotic protein BclxL and decrease in levels of p27/Kip1 cyclin dependent kinase inhibitor, both known EGFR targets (FIG. 4C, D). Again, these effects were inhibited by annexin V-mediated blockade of the microvesicle uptake by the acceptor U373 cells. Similar EGFRvIII-dependent changes in expression of other EGFRvIII target genes, e.g. p21/Cip, were also observed.

Figure 2:
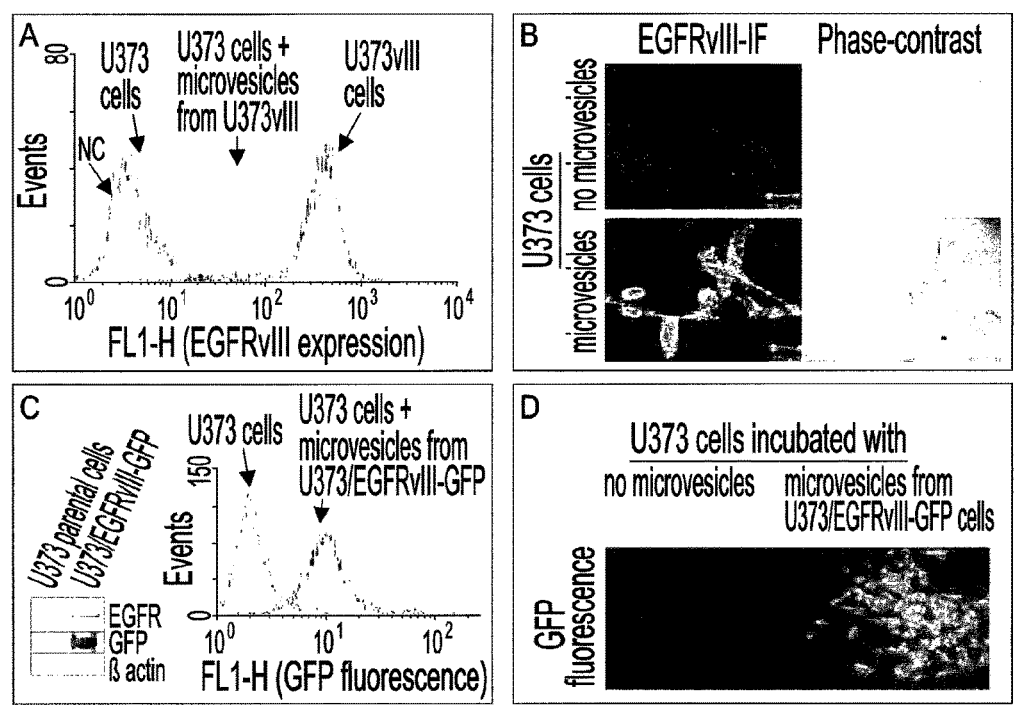
FIG. 2 illustrates the microvesicular transfer of the oncogenic EGFRvIII between glioma cells, wherein in (A) it is shown that U373 cells incubated with microvesicles released by their EGFRvIII-transformed counterparts (U373vIII) acquired the expression of the EGFRvIII antigen on their surface (FACS); in (B) the detection of EGFRvIII on the surface of U373 cells incubated with U373vIII-derived microvesicles is shown; in (C) the generation of the U373/EGFRvIII-GFP cell line by expression of the GFP-tagged EGFRvIII in U373 cells is observed; and in (D) the direct GFP-fluorescence of U373 cells incubated with EGFRvIII-GFP containing microvesicles is observed.
Figure 4:
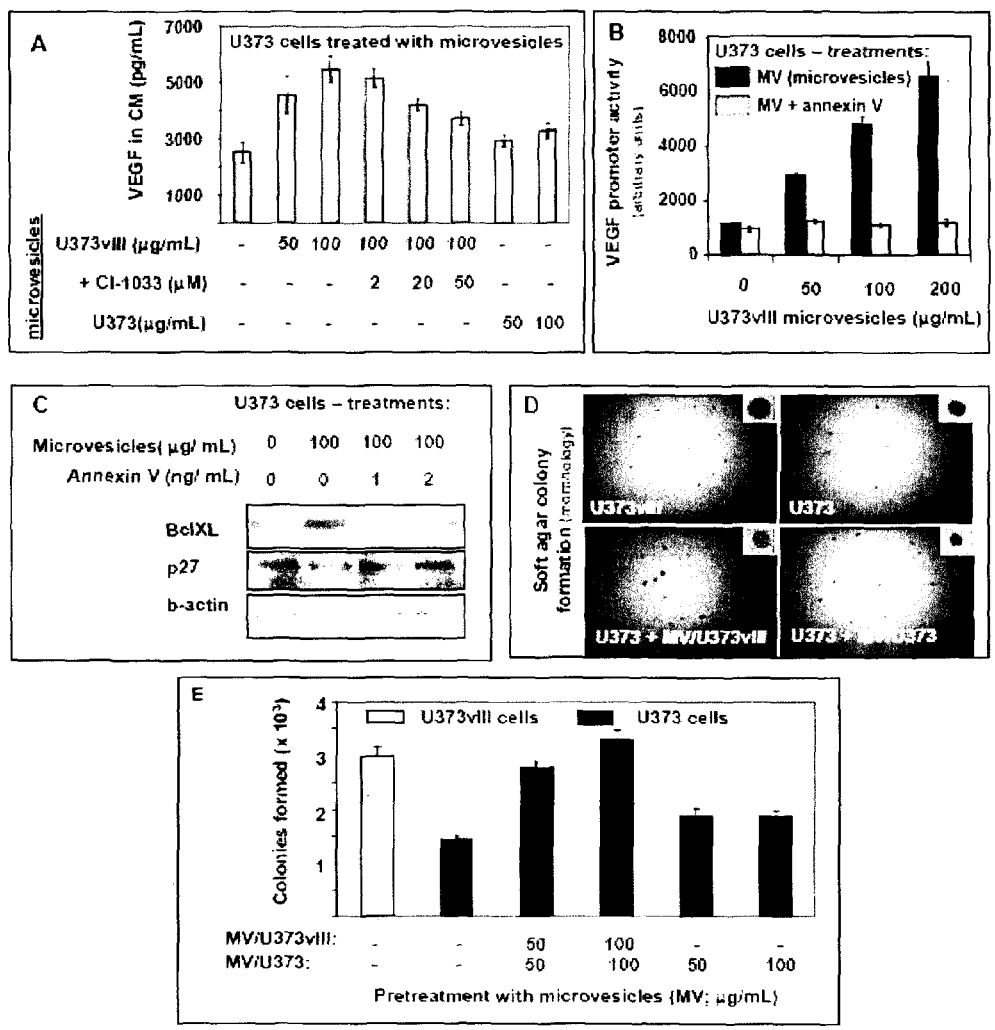
FIG. 4 illustrates the induction of cellular transformation by the uptake of EGFRvIII-containing microvesicles, wherein in (A) EGFRvIII-dependent increase in VEGF secretion by U373 cells that have incorporated U373vIII microvesicles is shown; in (B) it is shown that the stimulation of VEGF promoter activity in U373 cells by incorporation of EGFRvIII containing microvesicles can be blocked by pretreatment with annexin V; in (C) the increase in expression of BclxL (prosurvival), and reduced expression of p27 (cell cycle inhibitor) in U373 cells exposed to EGFRvIII containing microvesicles is shown, and in (D-E) it is observed the increase in soft agar colony forming capacity of U373 cells after pretreated with EGFRvIII containing microvesicles.

The functional consequences of the aforementioned repertoire of molecular responses evoked by incorporation of EGFRvIII-containing microvesicles can lead to a higher degree of cellular transformation, as demonstrated by more spindle morphology of U373 cells exposed to this material (FIG. 2B). U373 cells were preincubated with EGFRvIII containing microvesicles and tested for growth in semisolid media, a paradigmatic transformation assay. Remarkably, incorporation of the oncoprotein in this manner caused a twofold increase in anchorage independent soft agar colony formation of by U373 cells, while exposure to equivalent amounts of microvesicles devoid of EGFRvIII content was inconsequential (FIG. 4 D, E).

Figure 6:
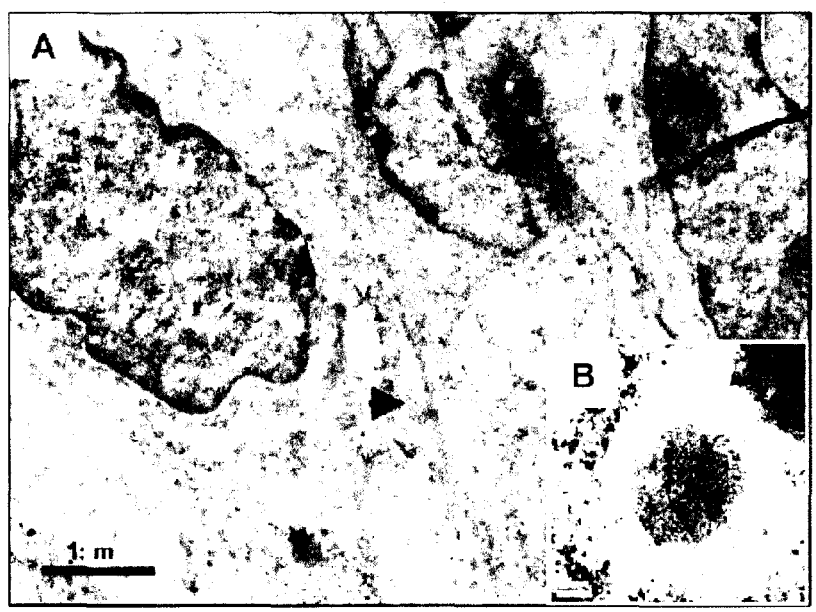
FIG. 6 illustrates microvesicle-like structures in vivo, wherein in (A) Transmission Electron Micrograph of microvesicular structures present in the intercellular space between two cancer cells (black arrow) within the mixed tumor xenograft in the SCID mouse are shown (bar—1 µm); and in (B) immunogold staining for EGFRvIII reveals the presence of this receptor (white arrow) in association with the microvesicles-like structures found within mixed U373vIII/U373-GFP tumors (bar—100 nm)
Figure 7:
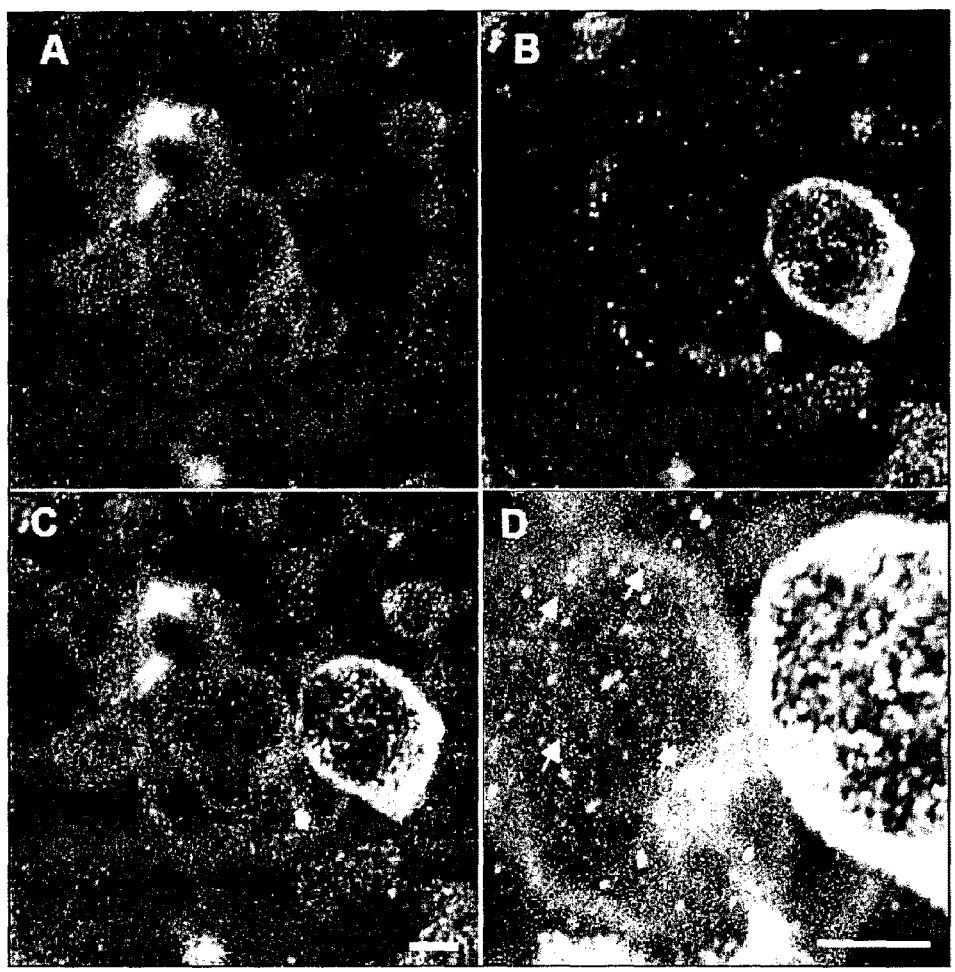
FIG. 7 illustrates emission of the FLAG/EGFRvIII-positive material from U373vIII cells in mixed tumors in vivo wherein photographic representation are shown of confocal microscopy of mixed tumors composed of U373-GFP (green) and U373vIII-FLAG glioma cells (red) and stained for GFP (green, panel A) and FLAG (red, panel B), respectively; merged channels (C and D) reveal the presence of the FLAG/EGFRvIII-positive microvesicle-like structures (arrows) which are associated not only with overtly FLAG/EGFRvIII-positive cells (U373vIII-FLAG, right side of panels C and D), but also with GFP-positive (U373-GFP) cells (bars—5 µm).

It is well recognized that in human GBMs, only a small sub-population of tumor cells harbor the primary genetic mutation leading to EGFRvIII expression, though there is increased growth of the entire tumor. In this regard, it is disclosed herein that EGFRvIII expression provokes formation of cellular microvesicles, to which this transmembrane protein becomes incorporated and shed to the pericellular micromilieu (FIGS. 6 and 7) and blood (FIG. 1F). The experiments disclosed herein demonstrate that microvesicles containing such an active oncogene (oncosomes) may serve as vehicles for rapid intercellular transfer of the transforming activity between cells populating brain tumors. This could lead to a horizontal propagation of an increased proliferative, survival and angiogenic capacity even without (prior to) enrichment in cells harbouring the respective mutation. This hitherto unappreciated form of Intercellular interaction is fundamentally different than the previously postulated transfer of DNA fragments containing oncogenic sequences from apoptotic cancer cells to their non-transformed (phagocytic) counterparts. Microvesicle exchange is also different from paracrine effects induced by secretion of tumor-stimulating soluble ligands, but it could amplify/modulate the latter effects by intercellular sharing of membrane-associated (and thereby insoluble) active receptors.

Figure 5:
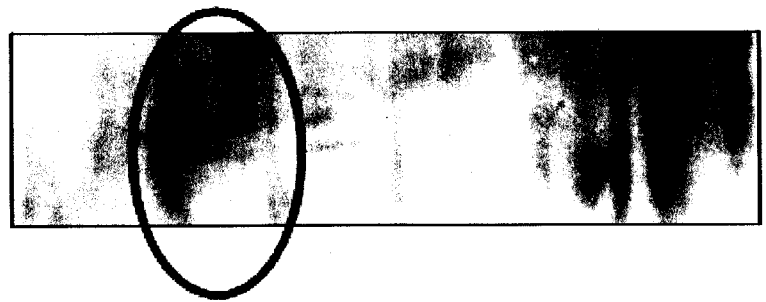
FIG. 5 illustrates a western blot analysis of blood-borne microvesicles wherein the detection of circulating EGFRvIII from blood samples of 6 patients (lanes 1 to 6) with glioblastoma multiforme is demonstrated for patient 2 (circled bands) and potentially for patient 3.

Confirming that in human GBMs, only a small subpopulation of tumor cells harbor the primary genetic mutation leading to EGFRvIII expression, both wild type EGFR and EGFRvIII bands were detected at the expected sizes and resolved using a standard SDS-PAGE protocol in microvesicles collected from human plasma of patients with GBM (FIG. 5).

It is encompassed that similar microvesicular transfer can also involve other transforming, mutant, upregulated, or otherwise activated membrane-associated oncogenic tyrosine kinases (e.g. HER-2, wtEGFR, cKit or MET) and proteins operative in a variety of human tumors. Host cells (e.g. endothelium) may also be targets of oncogene-containing microvesicles. In one aspect, the tumor promoting functions (e.g. angiogenesis) of a host cell could be exacerbated by microvesicular transfer. Conversely, tumor-associated host cells are often profoundly altered and their derived microvesicles (e.g. containing tumor endothelial markers (TEMs) of endothelial cells) could possess diagnostic, prognostic and predictive value.

It is also encompassed herein that agents capable of blocking exchange of microvesicles between cells (e.g. annexin V derivatives) may be useful as therapeutic agents, e.g. to inhibit cancer spreading and growth by inhibiting the fusion of microvesicles with cells. In an embodiment, methods for treating cancer are provided comprising administration of a microvesicle exchange blocking agent, e.g. annexin V and/or derivatives thereof, to a subject in need thereof. It is contemplated that any agent that could be used for blocking microvesicle, microparticle, ectosome or exosome transfer can be used in the methods of the inventions described herein. Other non-limiting examples of such agents include agents blocking P-selectin or its ligand, PSGL.

In another aspect, the invention provides methods of diagnosing cancer by allowing detection of multiple oncogenic proteins in microvesicles. For example, a cancer could be characterized by determining whether it carries EGFRvIII, HER-2, wtEGFR, cKit or MET, alone or in combination, by analyzing the protein composition of the microvesicles. The number of oncogenic protein-containing microvesicles found in a bodily fluid can also be used as a way of determining the aggressiveness of a tumor, i.e. its tendency to spread or metastasize. The methods of the invention can thus aid in diagnosis and/or prognosis. In one embodiment, diagnosis and/or prognosis of breast cancer can be determined by detecting the presence of EGFR and/or HER-2. In another embodiment, diagnosis and/or prognosis of tumors is determined by detecting the presence of HER-2 and/or HER-3.

In another embodiment, the invention provides methods of monitoring the progression of a cancer and/or monitoring the effectiveness of a treatment or therapeutic regimen. For example, the size and the nature of a tumor can be followed by monitoring the amount and composition of an oncogenic protein or proteins, e.g. EGFRvIII, HER-2, HER-3, cKit or MET, released in microvesicles. It would be expected, for example, that a larger tumor would include more cells and therefore release more microvesicles than a smaller one. This could be used to monitor therapy by providing a means to measure a change in size of a tumor, which may either shrink, grow, or stay the same. Such methods would be valuable in evaluating the effectiveness of a therapy in a patient population as a whole, or in an individual patient. It is also contemplated that the progression of a cancer and/or the response to treatment can be monitored by measuring a combination of oncogenic proteins found in microvesicles. In an embodiment, EGFR and HER-2 can be measured in combination, for example in breast cancer, thereby providing indication as to genetic status and progression (or recurrence) of malignancy, in some aspects irrespectively of the actual tumor size. In other embodiments, HER-2 and HER-3 or HER-2 and EGFR can be measured in combination, for example. Furthermore, as microvesicles may contain intact oncoproteins, in another embodiment the phosphorylation status of the oncoproteins can be determined to monitor or measure the efficacy of targeted treatments. For instance, monitoring the phosphorylation status of the EGFR/HER-2 combination in microvesicles derived from breast cancer could indicate the efficacy of a HER-2-directed drug such as Herceptin®, an EGFR-directed drug such as Tarceva®, or similar anti-cancer treatments, alone or in combination. In another aspect, the molecular environment surrounding an oncogenic protein in the microvesicles, e.g. other molecules, the entire proteome, or the phosphoproteome, may be used to monitor the progression of cancer and/or efficacy of an anti-cancer treatment. For example, the presence or absence or phosphorylation status of PTEN in the microvesicles may be indicative of progression or cancer and/or efficacy of an anti-cancer treatment.

In a further aspect, the invention provides methods of monitoring the progression of a cancer and/or monitoring the efficacy of an anti-cancer treatment or therapeutic regimen. It is contemplated that any anti-cancer treatment or therapeutic regimen known in the art could be used in the methods described herein. Non-limiting examples of treatments and therapeutic regimens encompassed herein include surgery, radiology, chemotherapy, and administration of targeted cancer therapies and treatments, which interfere with specific mechanisms involved in carcinogenesis and tumour growth. Non-limiting examples of targeted cancer therapies include therapies that inhibit tyrosine kinase associated targets (such as Iressa®, Tarceva® and Gleevec®), inhibitors of extracellular receptor binding sites for hormones, cytokines, and growth factors (Herceptin®, Erbitux®), proteasome inhibitors (Velcade®) and stimulators of apoptosis (Genasens®). Such targeted therapies can be achieved via small molecules, monoclonal antibodies, antisense, siRNA, aptamers and gene therapy. A subject may also receive a combination of treatments or therapeutic regimens. Any other treatment or therapeutic regimen known in the art can be used in the methods described herein, alone or in combination with other treatments or therapeutic regimens.

In another aspect, the invention provides methods of diagnosing cancer by allowing detection of multiple phosphorylated oncogenic proteins in microvesicles. In another embodiment, the invention provides methods of monitoring the progression of a cancer and/or monitoring the effectiveness of a treatment or therapeutic regiment by measuring the phosphorylation state of an oncogenic protein in the microvesicles.

Receptor tyrosine kinases (RTK), such as EGFR, contain an extracellular ligand binding domain connected to a cytoplasmic domain by a single transmembrane helix. The cytoplasmic domain contains a conserved protein tyrosine kinase core and additional regulatory sequences that are subject to autophosphorylation and phosphorylation by heterologous protein kinases. When a ligand binds to the extracellular domain of an RTK, dimerisation of the RTK with other adjacent RTKs is triggered. Dimerisation leads to a rapid activation of the proteins' cytoplasmic kinase domains, the first substrate for these domains being the receptor itself. As a result the activated receptor becomes autophosphorylated on multiple specific intracellular tyrosine residues. The phosphorylation of specific tyrosine residues within the activated receptor creates binding sites for Src homology 2 (SH2) and phosphotyrosine binding (PTB) domain containing proteins. Specific proteins containing these domains include Src and phospholipase Cγ, and the phosphorylation and activation of these two proteins upon receptor binding leads to the initiation of signal transduction pathways. Other proteins that interact with the activated receptor act as adaptor proteins and have no intrinsic enzymatic activity of their own. These adaptor proteins link RTK activation to downstream signal transduction pathways, such as the MAP kinase signalling cascade. The activity of virtually all RTKs can be enhanced, even in the absence of ligand binding, by treatment of cells with protein tyrosine phosphatase inhibitors. Thus, the persistent activation of a RTK, or an oncogenic receptor, that triggers abnormal expression of genes involved in cell proliferation, survival and angiogenesis, is positively regulated by one or several phosphotyrosine sites in the activation loop.

Phosphorylation of RTKs can be measured using a number of methods. Non-limiting examples of such methods include phosphospecific antibodies, staining with antibodies against phosphotyrosine residues, and direct kinase assays with phosphorylatable substrates. Another way to determine the phosphorylation status of multiple receptors on microvesicles could be to assess their total phosphoproteome using mass spectrometer (MS) related methods. It is contemplated that standard techniques known in the art for measuring and detecting phosphorylated proteins and the phosphorylation state of a protein can be used in the methods described herein.

The present invention will be more readily understood by referring to the following examples, which are given to illustrate the invention rather than to limit its scope.

EXAMPLE 1

Cell Culture and Isolation of Microvesicles

U373 (human astrocytoma) cells, their stable variant U373vIII expressing Tet-off regulated EGFRvIII or EGFRvIII fused at C-terminus to green fluorescent protein (pEGFPN1) cassette (U373vIII-GFP) and A431 are maintained as described previously (Viloria-Petit et al Am. J. Pathology, 1997, 6:1523-1530; Yu et al., 2005, Blood, 105: 1734-1741) in medium containing microvesicle-depleted fetal bovine serum FBS. HUVEC cells are maintained in EGM-2 (Cambrex Bioscience, Walkesville, Md., USA). Microvesicles are collected from conditioned media or mouse plasma, as previously described (Al-Nedawi et al., 2005, Arterioscler. Thromb. Vasc. Biol., 25: 1744-1749). Briefly, media are subjected to two successive centrifugations at 300 g and 12000 g to eliminate cells and debris. Microvesicles are pelleted by ultracentrifugation for 2 hours at 100 000 g and quantified by protein content and analyzed for EGFR or EGFRvIII content. For scanning electron microscopy (SEM) the cells are grown on cover slips, fixed with 2.5% gluteraldehyde, stained with 1% OsO4, covered with gold and visualized using the JEOL 840A instrument. For in vivo analyses tumors are generated by injection of $1-10 \times 10^6$ U373vIII or U373 cells into immunodeficient (SCID) mice (Charles River, Canada). In some cases mice are treated daily with the pan-ErbB inhibitor CI-1033 as indicated. Blood is collected from tumor bearing, or control mice by cardiac puncture into heparinized syringes. Platelet-free plasma is used to prepare microvesicles.

Flow cytometry (FACS) is employed to detect EGFRvIII, or EGFRvIII-GFP on the surface of viable not permeabilized cells and is carried out either with cells that expressed these receptors endogenously, or with those that have acquired such expression upon transfer of microvesicles. Typically. U373 cells are treated, with microvesicles (MVs) obtained from U373vIII or U373vIII-GFP cells for 24 hours. The cells are then detached using 2 mM EDTA (ethylenediaminetetraacetic acid) to obtain a single-cell suspension the aliquots of which ($1.5 \times 10^6$/sample) are washed in phosphate-buffered saline (PBS) with 1% FBS and 0.1% sodium azide. The cells treated with U373vIII derived MVs are then stained for 30 minutes at 4° C. with for example a monoclonal antibody against EGFRvIII (Zymed). After washing, samples are incubated with Alexa Fluor 488 goat anti-mouse secondary antibody (Molecular Probes, Eugene, Oreg.) for 30 minutes at 4° C., washed with phosphate buffered saline (PBS) and analyzed. In the case of treatment with MVs derived from U373vIII-GFP cells fresh cell suspensions are directly analyzed for GFP fluorescence. The data can be acquired using FACScalibur flow cytometer (BD Biosciences, Mountain View, Calif.).

All in vivo experiments are performed in 6- to 8-week-old severe combined immunodeficiency (SCID) mice (Charles River, Saint-Coustant, QC, Canada). Briefly, 1 to $10 \times 10^6$ of U373vIII or U373, cells are injected subcutaneously in 0.2 ml PBS. Blood is collected from mice by cardiac puncture, into heparin sodium solution. Platelet-free plasma was prepared by centrifugation at 2000 g for 15 minutes, 2000 g for 5 minutes, and 16,000 g for 5 minutes to isolate microvesicles.

EXAMPLE 2

Microvesicle Transfer Assays

U373 (acceptor) cells are treated with microvesicles for 24 hours and a single-cell suspension is analyzed by flow cytometry or fluorescent microscopy for expression of EGFRvIII or GFP. To detect signaling events, U373 are starved in 0.5% FBS (DMEM) before addition of microvesicles, which are either intact or preincubated with annexin-V, or CI-1033, at the concentrations as indicated. The expression of microvesicle associated molecules (EGFRvIII, TF), and expression of total and activated MAPK and Akt as well as other changes are assayed by immunoblot (BclxL, p27/Kip1), ELISA (VEGF, R&D Systems), or promoter activity assays (VEGF), as described elsewhere (Lopez-Ocejo et al. 2000, Oncogene, 40:4611-4620). For soft agar colony formation assays single cell suspensions are prepared in 0.3% agarose from equal numbers of cells pretreated with microvesicles or control media. Cultures are established in plates precoated with 0.5% agarose and all colonies containing more than 4 cells are counted.

EXAMPLE 3

Detection of Circulating EGFRvIII in Patients with Glioblastoma Multiforme

Microvesicles are collected from human plasma in a similar manner as previously described for plasma of tumor bearing mice (Al-Nedawi et al., 2008, Nature Cell Biology, 10: 619-624). Briefly, archival blood samples are subjected to two consecutive centrifugations at 300 g for 5 minutes, and then at 12000 g for 20 minutes to eliminate cells and debris. Finally, microvesicles are obtained after centrifugation for 2 hours at 100 000 g, washed twice with a large volume of phosphate buffered saline (PBS). The protein lysates are prepared in the lysis buffer containing: 10 mMTris, pH 6.8, 5 mM EDTA, 50 mM NaF, 30 mM sodium pyrophosphate, 2% (wt/vol) SDS, 1 mM phenylmethylsulfonyl fluoride (PMSF), and 1 mM $Na_3VO_4$, for 10 minutes on ice. Unless otherwise indicated the lysates are resolved by SDS-PAGE and subjected to immunoblotting with for example a mouse or a sheep anti-human EGFR polyclonal antibody or appropriate mouse monoclonal antibodies. Immunodetection is accomplished using the appropriate HRP-conjugated secondary antibody and chemiluminescence plus kit (ECL kit; Amersham Pharmacia, Buckinghamshire, United Kingdom), after which the blots are scanned and protein bands quantified using for example the Storm 860 scanner (GE healthcare). Both wild type EGFR and EGFRvIII bands are detected in this manner at the expected sizes and resolved using a standard SDS-PAGE protocol.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method comprising:
   a) collecting a first sample from a subject having glioma at a first timepoint, isolating microvesicles from the first sample, and measuring EGFRvIII in the microvesicles obtained from the first sample; and
   b) collecting a second sample from the subject having glioma at a second timepoint, the second timepoint occurring after the first timepoint, isolating microvesicles from the second sample, and measuring EGFRvIII in the microvesicles obtained from the second sample,
   wherein the first timepoint occurs before the subject has received an anti-cancer treatment, and the second timepoint occurs after the subject has received the anti-cancer treatment.

2. The method according to claim 1, further comprising the step of measuring the phosphorylation state of EGFRvIII.

3. The method according to claim 1, wherein there is an increase in the amount of EGFRvIII in the microvesicles obtained from the second sample compared to the amount of EGFRvIII in the microvesicles obtained from the first sample.

4. The method according to claim 1, wherein there is a reduction in the amount of EGFRvIII in the microvesicles obtained from the second sample compared to the amount of EGFRvIII in the microvesicles obtained from the first sample.

5. The method according to claim 1, wherein there is no change in the amount of EGFRvIII in the microvesicles obtained from the second sample compared to the amount of EGFRvIII in the microvesicles obtained from the first sample.

6. The method according to claim 1, wherein said sample is a bodily fluid.

7. The method of claim 6, wherein said body fluid is selected from the group consisting of blood, lymph, urine, cerebrospinal fluid, ascites, saliva, lavage, semen, glandular secretions, exudate, contents of cysts and feces.

8. The method according to claim 1, further comprising measuring an oncogenic protein in the microvesicles, wherein the oncogenic protein is selected from the group consisting of MET, cKit, PDGFR, Wnt, beta-catenin, K-ras, H-ras, N-ras, Raf, N-myc, c-myc, IGFR, PI3K, Akt, BRCA1, BRCA2, PTEN, and receptors of cancer associated cells selected from the group consisting of VEGFR-2, VEGFR-1, Tie-2, TEM-1 and CD276.

9. The method according to claim 1, wherein the microvesicles are isolated by ultracentrifugation, immunoprecipitation or microfiltration.

10. The method according to claim 1, wherein the presence of EGFRvIII in the microvesicles is detected or measured by immunoblot, immunoprecipitation, ELISA, RIA, flow cytometry, electron microscopy or mass spectrometry.

11. The method according to claim 1, wherein the microvesicles are detected or measured by ELISA with wells coated with Annexin V.

12. The method according to claim 1, wherein the anti-cancer treatment is surgery, radiology, chemotherapy, a targeted cancer treatment, or a combination thereof.

* * * * *